United States Patent
Ilic et al.

(10) Patent No.: US 7,409,851 B2
(45) Date of Patent: Aug. 12, 2008

(54) DETECTION OF SMALL BOUND MASS

(75) Inventors: Bojan (Rob) Ilic, Ithaca, NY (US); Harold G. Craighead, Ithaca, NY (US)

(73) Assignee: Cornell Research Foundation, Inc., Ithaca, NY (US)

(*) Notice: Subject to any disclaimer, the term of this patent is extended or adjusted under 35 U.S.C. 154(b) by 207 days.

(21) Appl. No.: 11/093,008

(22) Filed: Mar. 29, 2005

(65) Prior Publication Data

US 2006/0219010 A1  Oct. 5, 2006

(51) Int. Cl.
*G01N 29/02* (2006.01)

(52) U.S. Cl. .............. 73/24.06; 73/24.01; 73/32 A; 73/61.75; 73/64.53; 436/518; 422/82.01

(58) Field of Classification Search .............. 73/24.01, 73/24.06, 32 A, 61.75, 64.53; 436/518
See application file for complete search history.

(56) References Cited

U.S. PATENT DOCUMENTS

| | | | | |
|---|---|---|---|---|
| 7,207,206 | B2* | 4/2007 | Pinnaduwage et al. | 73/23.2 |
| 2002/0166962 | A1* | 11/2002 | Roukes et al. | 250/306 |
| 2003/0024823 | A1* | 2/2003 | Ferguson et al. | 205/317 |
| 2004/0152211 | A1* | 8/2004 | Majumdar et al. | 436/518 |
| 2006/0257286 | A1* | 11/2006 | Adams | 422/82.01 |
| 2007/0158553 | A1* | 7/2007 | Roukes | 250/309 |

FOREIGN PATENT DOCUMENTS

WO  WO 03/095616 A2 * 11/2003

OTHER PUBLICATIONS

Carr, D., "Fabrication of Nanoelectromechanical Systems in Single Crystal Silicon Using Silicon on Insulator Substrates and Electron Beam Lithography", *Journal of Vacuum Science & Technology B*, 15(6), (1997),2760-2763.

Carr, D. W., "Measurement of Mechanical Resonance and Losses in Nanometer Scale Silicon Wires", *Applied Physics Letters*, 75(7), (1999), 920-922.

Craighead, H G., "Nanoelectromechanical Systems", *Science*, 290(5496), (Nov. 24, 2000), 1532-1535.

Flink, S. , et al., "Sensor Functionalities in Self-Assembled Monolayers", *Advanced Materials*, 12(18), (2000), 1315-1328.

Fritz, J. , "Translating Biomolecular Recognition into Nanomechanics", *Science*, 288(5464), (Apr. 14, 2000), 316-318.

(Continued)

*Primary Examiner*—Hezron E. Williams
*Assistant Examiner*—Rose M Miller
(74) *Attorney, Agent, or Firm*—Schwegman, Lundberg & Woessner, P.A.

(57) ABSTRACT

Prefabricated catalyzing adsorption sites are incorporated into small oscillators. In one embodiment, the sites are formed of precisely positioned gold anchors on surface micromachined oscillators. The micromachined oscillators may be formed of silicon, such as polysilicon, or silicon nitride in various embodiments. The sites allow special control of chemical surface functionality for the detection of analytes of interest. Thiolate molecules may be adsorbed from solution onto the gold anchors, creating a dense thiol monolayer with a tail end group pointing outwards from the surface of the gold anchor. This results in a thiolate self-assembled monolayer (SAM), creating a strong interaction between the functional group and the gold anchor.

22 Claims, 19 Drawing Sheets

OTHER PUBLICATIONS

Hu, Z., et al., "Investigation of Adsorption and Absorption-Induced Stresses Using Microcantilever Sensors", *Journal of Applied Physics*, 90(1), (Jul. 1, 2004), 427-431.

Huang, X. M., et al., "Nanodevice Motion at Microwave Frequencies", *Nature*, 421(6922), (Jan. 30, 2003), p. 496.

Ilic, B., et al., "Mechanical Resonant Immunospecific Biological Detector", *Applied Physics Letters*, 77(3), (Jul. 17, 2000), 450-452.

Ilic, B., et al., "Single Cell Detection With Micromechanical Oscillators", *Journal of Vacuum Science & Technology B*, 19(6), (Nov./Dec. 2001), 2825-2828.

Lang, H. P., "Sequential Position Readout From Arrays of Micromechanical Cantilever Sensors", *Applied Physics Letters*, 72(3), (1998), 383-385.

Meyer, G., "Novel Optical Approach to Atomic Force Microscopy", *Applied Physics Letters*, 53(12), (Sep. 19, 1988), 1045-1047.

Newell, W. E., "Miniaturization of Tuning Forks", *Science*, 161(3848), (Sep. 27, 1968), 1320-1326.

Petersen, K. E., "Silicon as a Mechanical Material", *Proceedings of the IEEE*, 70(5), (May 1982), 420-446.

Pinnaduwage, L. A., et al., "Sensitive Detection of Plastic Explosives With Self-Assembled Monolayer-Coated Microcantilevers", *Applied Physics Letters*, 83(7), (Aug. 18, 2003), 1471-1473.

Senaratne, W., et al., "Dinitrophenyl Ligand Substrates for Piezoelectric Analysis of Bio-Specificity in Antibody Based Biosensors", *Abstracts, 31st Northeast Regional Meeting of the American Chemical Society*, (Abstract Only), (2003), 1 pg.

Subramanian, A., et al., "Glucose Biosensing Using an Enzyme-Coated Microcantilever", *Applied Physics Letters*, 81(2), (Jul. 8, 2002), 385-387.

Tsutsumi, H., et al., "Electrochemical Behavior of a 4-Nitrothiophenol Modified Electrode Prepared by the Self-Assembly Method", *Journal of Colloid and Interface Science*, 171, (1995), 505-511.

Ulman, A., "Formation and Structure of Self-Assembled Monoloyers", *Chemical Reviews*, 96(4), (1996), 1533-1554.

Wachter, E. A., et al., "Micromechanical Sensors for Chemical and Physical Measurements", *Review of Scientific Instruments*, 66(6), (Jun. 1995), 3662-3667.

Yang, Y. T., et al., "Monocrystalline Silicon Carbide Nanoelectromechnical Systems", *Applied Physics Letters*, 78(2), (Jan. 8, 2001), 162-164.

* cited by examiner

US 7,409,851 B2

DETECTION OF SMALL BOUND MASS

GOVERNMENT FUNDING

The invention described herein was made with U.S. Government support under Grant Number ECS-9876771 awarded by NSF/NBTC. The United States Government has certain rights in the invention.

BACKGROUND

Interest in sensors and actuators and the availability of new fabrication approaches is leading to growing interest in micro- and nano-electromechanical systems (NEMS), oscillators, and resonant systems. One of the possible applications of NEMS resonant devices is sensitive detection of bound mass. Most earlier work has been devoted to the immobilization of target species onto the surface of the resonating structure. In such a scenario, pathogen-binding events alter the mechanical stress of the oscillator and its total mass and thus influence both the bending and the natural frequency of the cantilever. Signal transduction is generally achieved by employing an optical deflection (or interferometric) system to measure the mechanical bending or the frequency spectra resulting from additional loading by the adsorbed mass. Such systems generally do not achieve sufficient sensitivity to mass changes to reliably detect very small bound masses.

SUMMARY

Binding sites are prefabricated on localized areas of small oscillators. The binding sites provide an increased selectivity for a desired substance, allowing it's mass to be detected due to resonant frequency shifts of the oscillators. In one embodiment, prefabricated catalyzing adsorption sites are incorporated into small oscillators. The sites may be formed of precisely positioned gold anchors on surface micromachined oscillators. The micromachined oscillators may be formed of silicon, such as polysilicon, or silicon nitride in various embodiments. The sites allow special control of chemical surface functionality for the detection of analytes of interest. In various embodiments, the sites reduce the amount of non-specifically bound material, thus increasing sensitivity of mass measurements.

Arrays of oscillators or resonators may be fabricated using photolithographic processes, such as electron beam lithograph (EBL). The sites may be formed by evaporating gold. In one embodiment, Thiolate molecules may be adsorbed from solution onto the gold anchors, creating a dense thiol monolayer with a tail end group pointing outwards from the surface of the gold anchor. This results in a thiolate self-assembled monolayer (SAM), creating a strong interaction between the functional group and the gold anchor.

In further embodiments, selective amounts of gold may be removed form the gold anchors to obtain desired frequency response characteristics. Further, precise tailoring of the length of the alkane chain and chemical properties of both head and tail groups provide excellent systems for further engineering of the chemical surface functionality following assembly of the SAM.

In still further embodiments, vacuum encapsulation of the resonator is utilized to further increase the sensitivity of the resonator to a bound mass. Detection of masses in the attogram regime may be achieved, allowing detection of desired atoms. The prefabricated binding sites may be formed of different materials in further embodiments.

DETAILED DESCRIPTION

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description is, therefore, not to be taken in a limited sense, and the scope of the present invention is defined by the appended claims.

Figure 1A:
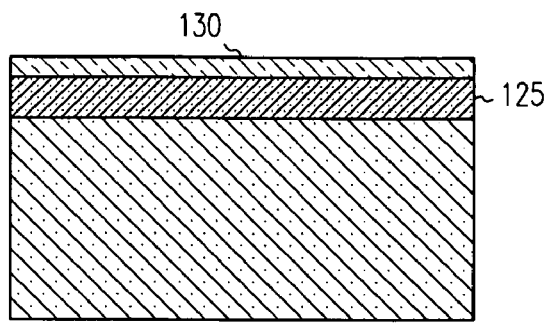
FIGS. 1A, 1B, 1C, 1D, 1E and 1F are diagrams showing formation of nanomechanical cantilever beam oscillators according to an example embodiment.
Figure 1B:
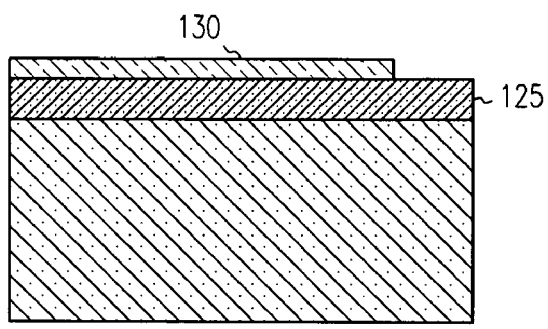
Figure 1C:
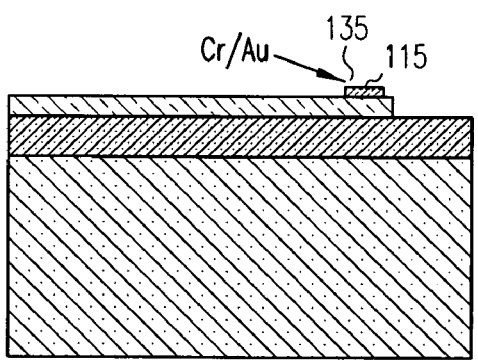
Figure 1D:
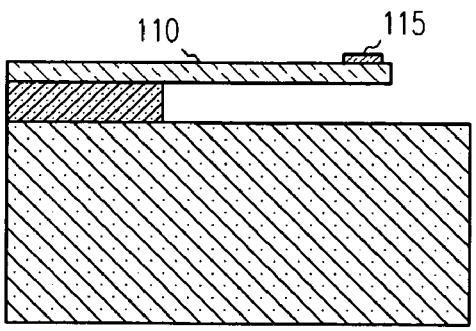

In one embodiment, electron-beam lithography (EBL) may be used to fabricate both polycrystalline silicon and silicon nitride resonators 110 with evaporated gold contact pads 115 as shown in FIGS. 1A-1F. In one embodiment the resonators are beam type cantilever resonators having a clamped end and a free end. Paddles 120 are formed on the free end of the resonators 110. FIG. 2 illustrates an array of dual clamped beam oscillators, also having gold contact pads on paddles formed midway between the clamped ends.

Figure 3:
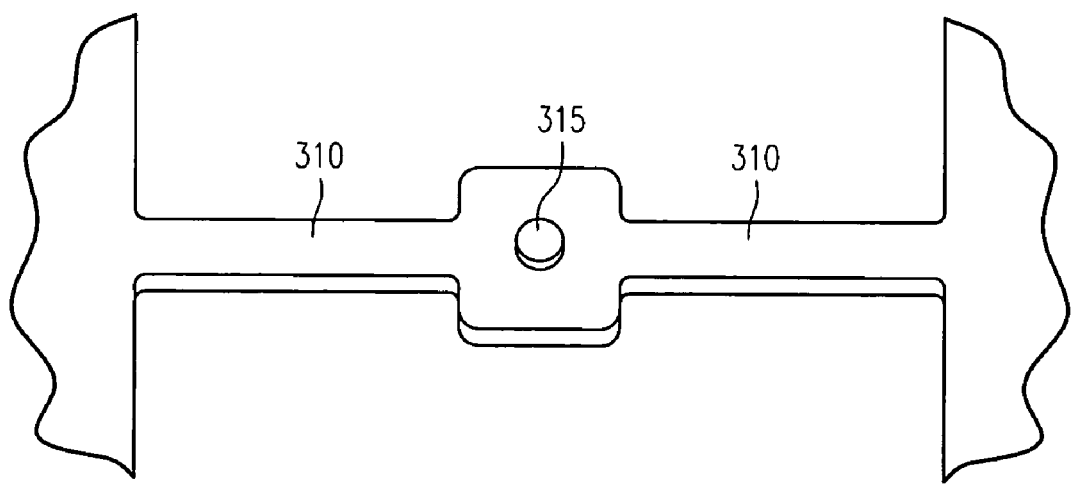
FIG. 3 is a perspective view of a dual clamped end nanomechanical beam with an adsorption site according to an example embodiment.

Thiolate molecules may subsequently be adsorbed from solution onto the Au contact pads, also referred to as anchors, creating a dense thiol self-assembled monolayer as shown in FIG. 3, with a tail end group pointing outwards from the surface. Other molecules may also be used as anchors, such as antibodies, proteins, thiolate modified DNA and others. Such molecules act as a catalyzing element that may be placed in close proximity to the most sensitive portion of the oscillator. The catalyst can be a magnetic material, noble metal, or some other material. An antibody can be functionalized with a group that attaches to the catalyst, which can then be further used to capture antigens or other substances.

A common feature of the thiolate self-assembled monolayer (SAM) systems is a strong interaction between the functional group and the gold contact pads. The van der Waals interactions among the molecules permit dense packing of the monolayer into a supermolecular hierarchical organization of interlocking components. Typically, the total amount of material in a well-packed alkanethiol SAM on gold is approximately $8.3 \times 10^{-10}$ mol cm$^{-2}$. Thiolate SAMs offer unique opportunities for precise tailoring of length of the alkane chain and chemical properties of both the head and tail groups, thus making them excellent systems for further engineering of the chemical surface functionality following the assembly of the SAM. Typical examples of reported functionalities of the tail group are $CH_3$, OH, COOH, CH=$CH_2$, C≡CH, and $CF_3$.

In one embodiment, the prefabricated gold contacts on the surface of the oscillators enable localized SAM binding to circular areas approximately 50-400 nm in diameter. Other size areas may also be used. Detection of the resonant frequency shift allows the determination of the mass of the adsorbed SAM. Frequency shift measurements may be calibrated by removal of a known mass of gold from the surface of the oscillator. Analytical calculations and finite element modeling are in good agreement with the experimental results in some embodiments. Additionally, control experiments showed high binding specificity of the thiolate SAM to the Au.

FIGS. 1A-1F illustrate the use of surface micromachining technology for fabrication of example resonating devices. Fabrication of the devices starts with clean 4 in. (100) silicon wafers. Other sized wafers may also be used, as a well as substrates formed of different materials. First, a 2-μm-thick thermally grown silicon dioxide layer 125 is formed. The $SiO_2$ layer 125 serves as sacrificial release layer that will be described in the following steps. Other sacrificial layer materials and thicknesses may also be used in further embodiments.

A device layer 130 consisting of either low-stress silicon nitride or amorphous silicon may be deposited using low-pressure chemical vapor deposition (LPCVD) in some embodiments. In the case of silicon nitride, internal and thermal stresses are low enough to attain freestanding nanomechanical structures. The device layer 130 may also be formed of other materials. Crystallization and stress-field alleviation from the amorphous silicon may be achieved by subsequent annealing at approximately 1050° C. for 15 min, for example. Other temperatures and times may also be utilized. Using wafer curvature methods, substantially complete stress relaxation may be obtained in the resulting polycrystalline silicon films.

I-line projection lithography with a gold lift-off may be performed to define 10 μm gold octagon pads 115 for use in alignment in subsequent EBL steps. Other types of methods may also be used to form the pads. EBL of other methods may be used to define the body of the oscillator 110. A hard etch-mask chromium layer 135 may deposited using electron-beam evaporation and lifted off. Other masks and methods of patterning may also be used. The device layer 130 may be etched down to the sacrificial oxide 125 using reactive ion etching in a $CF_4$ plasma chemistry, and the remaining chromium layer may be removed.

Figure 4:
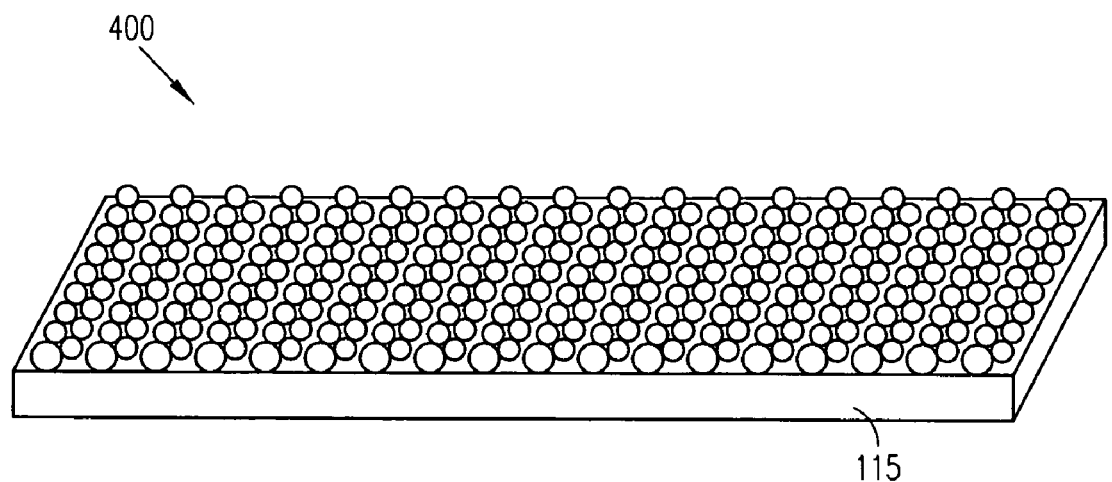
FIG. 4 is a schematic diagram of a fully assembled self-assembled monolayer on an adsorption site according to an example embodiment.

A bi-layer electron-beam resist process or other process may be used to define the biomolecular tethering sites 400, illustrated in FIG. 4. First, a solution of 4% concentration of 495 K molecular weight polymethyl methacrylate (PMMA) in anisole may be spun at 4000 rpm for 60 seconds, and baked in air at 170° C. for 15 min in one embodiment. Other resist processes may also be used. A 2% concentration of 950 K molecular weight PMMA in methyl isobutyl ketone (MIBK) may then be spun at 2000 rmp and baked at 170° C. for 15 min. The resist may be patterned using EBL (100 kV Leica VB6) and developed in MIBK: isopropyl alcohol 1:3 for 1 min. Placement accuracy of less than 10 nm may be achieved using die-by-die alignment.

In one embodiment, circularly exposed regions range from 50 to 400 nm in diameter. After the patterning, gold (15 nm) with a chromium (5 nm) adhesion layer may be deposited using electron-beam evaporation and subsequently lifted off in a solution of methylene chloride as shown in FIG. 1C. Devices may be released by etching the sacrificial oxide layer in hydrofluoric acid, washed in deionized water and isopropyl alcohol, and then nitrogen dried, resulting in the structure shown in FIG. 1D. Stiction may be observed for cantilever devices exceeding lengths of 20 μm with a thickness ranging between 160 and 250 nm. Other dimensions and processes may be used in further embodiments.

Figure 1E:
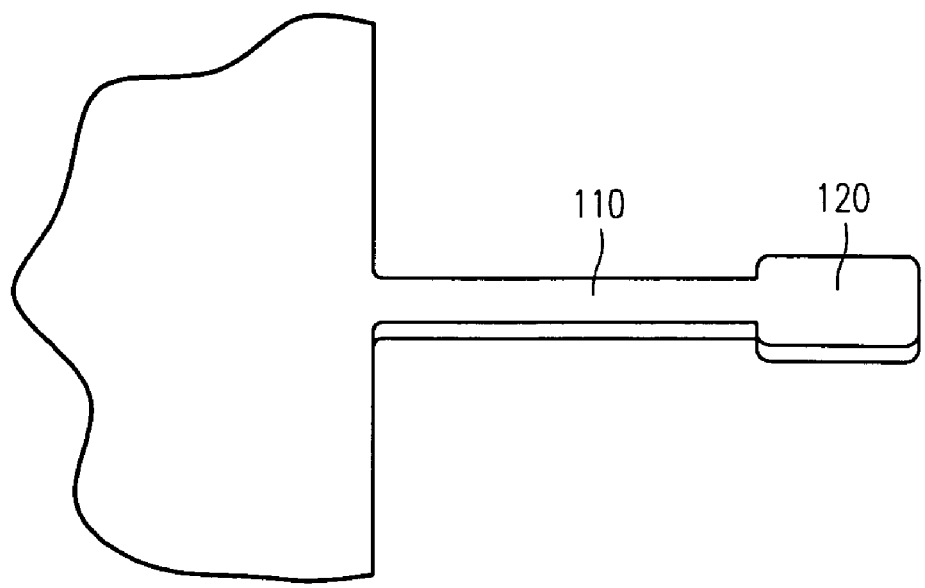
Figure 1F:
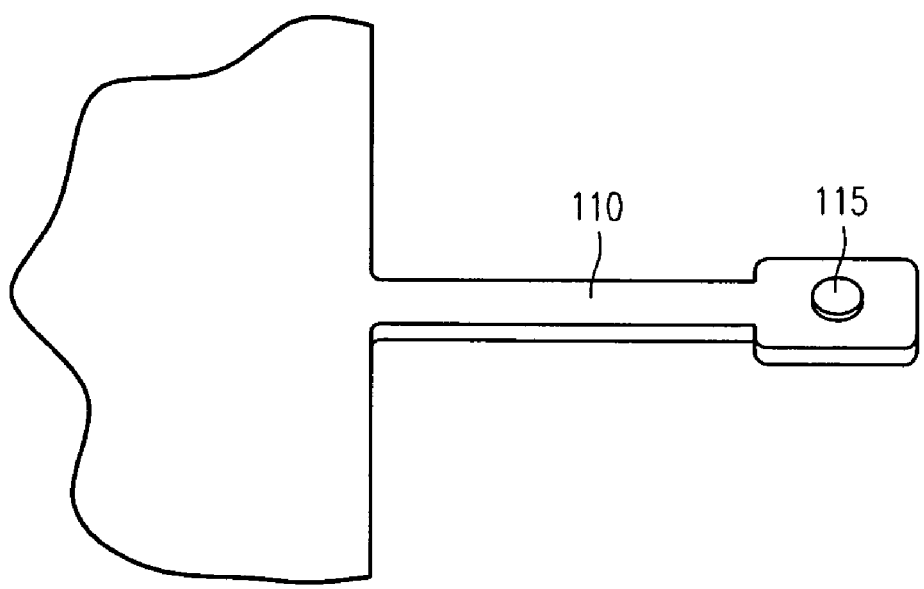
Figure 2:
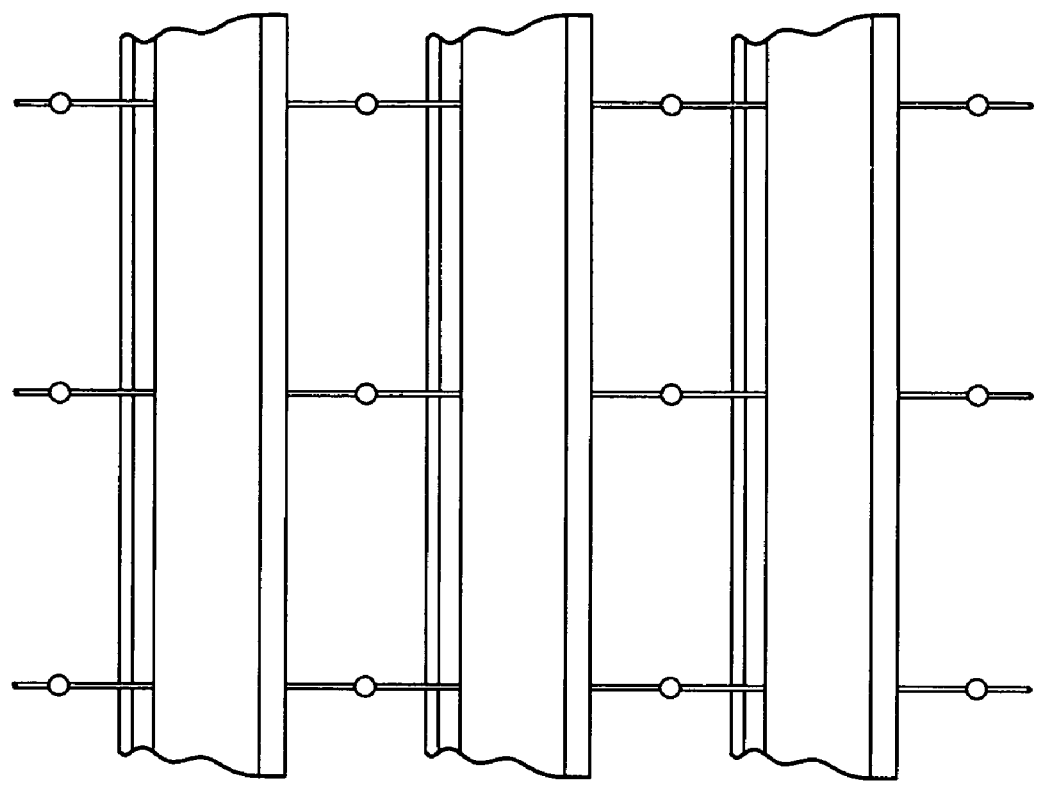
FIG. 2 is a perspective view of an array of nanomechanical beam oscillators according to an example embodiment.

FIGS. 1E and 1F show illustrations of released paddle-cantilevers used for control and mass measurements, respectively formed using the above processes. The resonant frequency of the cantilevers, operating as oscillators may be measured by thermo-optically driving the devices. An optical interferometric detection technique which may be used to measure displacement of these devices is diffraction spot limited. This limitation may be overcome by using the 1 μm×1 μm paddle 120 for narrow width oscillators. In one embodiment, a polycrystalline silicon beam resonator 110 may be 165 nm thick, 500 nm wide, and 4 μm long, with paddle 120 dimensions of 1 μm×1 μm and a gold pad 115 with a 250 nm diameter. In one embodiment, the gold pad is substantially centered on the paddle 120. Other dimensions and processes may be used in further embodiments.

An oblique-angle illustration of an example released device with circular Au dots or gold pads is shown at 310 in FIG. 3. In various embodiments, devices 310 may be fabricated from 250-nm-thick low-stress silicon nitride. In the case of the cantilevers, the width and length may be 1 and 10 μm, respectively. The device 310 is a doubly clamped oscillator with a width of 200 nm, length of 6 μm, and 1 μm×1 μm paddles. Au anchors 315 are positioned 500 nm from the edges of the device. The images show reasonably good alignment of the Au pads with respect to the center of the resonators. In various embodiments, the diameters of the Au pads may be varied. Example embodiments include pads with diameters of approximately 50 nm, 100 nm, 200 nm and 400 nm. Dimensions of the device 310 may also be varied significantly in further embodiments, consistent with a desired mass to be measured.

Dynamic frequency response characterization may be performed on various embodiments to evaluate the performance of the NEMS oscillators. Immediately following the release, measurements of the resonant frequency were conducted in a vacuum chamber for one example embodiment. First, 5-mm-square silicon chips were epoxied onto a 1-in.-diameter piezo transducers and placed into the vacuum chamber. In order to remove viscous damping mechanisms, a turbomolecular pump was used to evacuate the chamber to a pressure of $3 \times 10^{-6}$ Torr.

Baseline frequency spectra were acquired for various devices using an optical interferometric technique. An RF (radio frequency) spectrum analyzer with a tracking generator output, amplified by an RF power amplifier, was used to mechanically excite the NEMS structures and simultaneously measure the signal from the optical detector. The excitation signals, well below the nonlinear threshold, were applied. Example results confirm significant amplification of the out-of-plane translational vibration without both, influencing the eigenfrequency of the beam and causing degradation to the quality factor of the resonator.

Following the baseline measurements, devices were removed from the chamber and immersed in a thiol solution for 3 h. A dinitrophenyl poly(ethylene glycol) undecanthiol-based molecule (DNP-PEG4-C11 thiol) was used as a model ligand due to its interesting functional groups. In order to have an organized assembly, a gold self-assemblying fragment was incorporated into the ligand. Eleven carbon alkyl chains used for this purpose may give rise to flexibility and high packing density to the system. The thiol end group not only provides a good attachment site to gold, but gives chemical selectivity for reaction with gold over the device layer, reducing the possibility of physical adsorption.

The nitro groups can be used as redox active sites and hence used for detection using electrochemical methods. Using cyclic voltammetry on monolayers assembled on gold electrodes the surface coverage may be calculated using the redox active dinitro molecules on the substrate. Surface coverage may be calculated to be $2.7 \times 10^{-10}$ mol cm$^{-2}$. Theoretical data for the alkyl thiol assemblies on Au (111) are $7.8 \times 10^{-10}$ mol cm$^{-2}$ with data on DNP-containing thiols having values from $1.3 \times 10^{-10}$ mol cm$^{-2}$ for 4-nitrophenols to $1.5 \times 10^{-11}$ mol cm$^{-2}$ for dinitrospirans. This suggests that the incorporation of the DNP-PEG4-C11 thiols on gold to be reasonable, but has the possibility of leaving some unbound Au surface sites (pinholes) which is not uncommon.

A SAM forms within seconds, however, well-ordered, defect-free, high-quality SAMs are known to form after several hours. Thiol (S—H) head groups bind selectively to the Au surface creating a dense monolayer with a DNP-terminated tail group pointing outwards from the surface. FIG. 4 shows a schematic of a fully assembled SAM 400 on the surface of Au 115.

In one example, following self-assembly, devices were rinsed with methylene chloride, acetone, isopropyl alcohol and dried with nitrogen. Devices were then placed into the vacuum chamber and evacuated for 8 hours to a pressure of $3 \times 10^{-6}$ Torr. Experimental conditions identical to those during baseline measurements were met prior to measuring the frequency spectra. The acquired frequency shift was then correlated to the amount of adsorbed SAM.

In order to determine the sensitivity of the devices and validity of analytical models, sets of calibration experiments were performed. Devices with a known, prefabricated gold mass were wet etched using potassium iodide based chemistry. Devices were then rinsed, nitrogen dried, and subsequently placed into the vacuum chamber and measured. The resulting frequency shift with respect to the varying gold mass provided calibration curves for different oscillator geometries.

The following section describes the relevant theory used to analyze resonance of differently shaped NEMS structures and to determine the natural frequency to added mass relation. While the theory is presented, it is not required that the invention as claimed operate in accordance with the theory. In the analysis, several mechanical designs of beams with one end fixed and the other end free, and ones with both ends fixed were considered. The oscillator material is assumed linear, homogeneous, and isotropic. Since the beam is externally excited during experimental measurements, a kinematic excitation analysis showed a lack of influence of the drive mechanism on the eigenfrequency of the oscillator in the limit of small beam deflections. For the case of large deflections, where the motion of the beam is described by a nonlinear equation, the amplitude of the kinematic excitation can have an influence on the response frequency. To simplify matters, we assume that the response is linear and ensure linear regime operation by driving the oscillator with signal excitations more than an order of magnitude lower than the nonlinear threshold.

Cantilever Beam with a Concentrated Mass at the Free End

Figure 5:
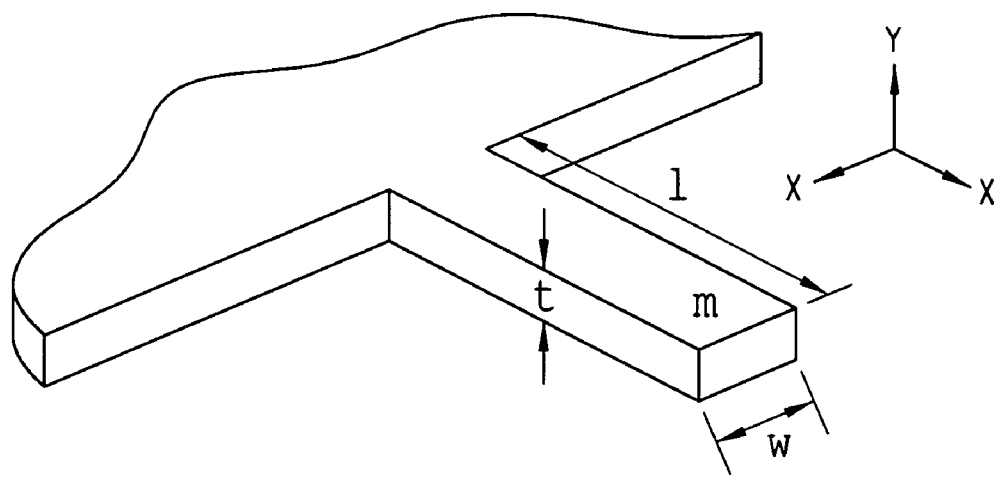
FIG. 5 is a schematic diagram of a cantilever with additional loading at the free end of the cantilever according to an example embodiment.

A first approach consisted of considering an additional mass loading effect imposed at the free end of a cantilever beam. In order to determine the frequency of a rectangular cantilever beam of length l, width w, and thickness t as seen in FIG. 5, the following homogeneous undamped equation is considered:

$$EI\frac{\partial^4 y}{\partial x^4} + \rho A \frac{\partial^2 y}{\partial t^2} = 0, \tag{1}$$

where E is the Young modulus of elasticity, I is the moment of inertia of the cantilever, y is the transverse displacement of the beam, $\rho$ is the mass density, and A is the cross-sectional area of the cantilever. By assuming time harmonic solutions $$[y=Y(x)e^{i\omega t}], \quad \text{Eq. (1)}$$

is reduced to $$\frac{d^4 Y}{dx^4} - \beta^4 Y = 0, \tag{2}$$

where $$\beta^4 = \omega^2 \left(\frac{\rho A}{EI}\right) \tag{3}$$

is the frequency parameter. The general solution to the equation of motion for a cantilever beam is given by $$Y(x) = C_1 \sin\beta x + C_2 \cos\beta x + C_3 \sinh\beta x + C_4 \cosh\beta x. \quad (4)$$

The following boundary conditions are imposed to determine the coefficients. At x=0, both the deflection and slope are zero:

$$C_2 + C_4 = 0, \quad (5)$$

$$C_1 + C_3 = 0. \quad (6)$$

Boundary conditions at x=l require the moment M to be zero and from dynamic equilibrium the shear V to be equal to $\omega^2$ my(l):

$$M = EI \frac{d^2 Y}{dx^2} = 0, \quad (7a)$$

$$-C_1(\sin\eta + \sinh\eta) - C_2(\cos\eta + \cosh\eta) = 0, \quad (7b)$$

$$V = -EI \frac{d^3 Y}{dx^3} = \omega^2 m Y(l), \quad (8a)$$

$$-C_1[\cos\eta + \cosh\eta - \gamma\eta(\sin\eta + \sinh\eta)] + \\ C_2[(\sin\eta + \sinh\eta) - \gamma\eta(\cos\eta + \cosh\eta)] = 0, \quad (8b)$$

where $\eta = \beta l$ and $\gamma = m/\rho Al$ is the dimensionless ratio of the concentrated mass (m) to the mass of the oscillator.

To have a nontrivial solution for the coefficients, it is required that $$(\cos\eta \cos h\eta + 1) + \gamma\eta(\sin h\eta \cos\eta - \cos h\eta)] = 0 \quad (9)$$

while the modes of vibration Y(x) are given by $$Y = C_1 \left[ \sin\beta x - \sinh\beta x + \frac{C_2}{C_1}(\cos\beta x - \cosh\beta x) \right], \quad (10a)$$

$$\frac{C_2}{C_1} = \frac{\cos\eta + \cosh\eta - \gamma\eta(\sin\eta - \sinh\eta)}{\sin\eta - \sinh\eta + \gamma\eta(\cos\eta - \cosh\eta)}, \quad (10b)$$

and C1 is chosen in such a way that Y(l)=1.

For arbitrary values of the mass ratio, there are multiple eigenfrequencies at which the transcendental equation is satisfied. Equation (9) was solved numerically to determine βl for a given dimensionless mass ratio γ. Rayleigh's quotient with the first natural mode of the beam Eq. (10a) without end mass (γ=0) as a trial function leads to the approximate expression for the natural frequency:

$$f_0 = \frac{(\tilde{\beta}l)^2}{2\pi} \frac{t}{l^2} \sqrt{\frac{E}{12\rho(1+4\gamma)}}. \quad (11)$$

Figure 6:
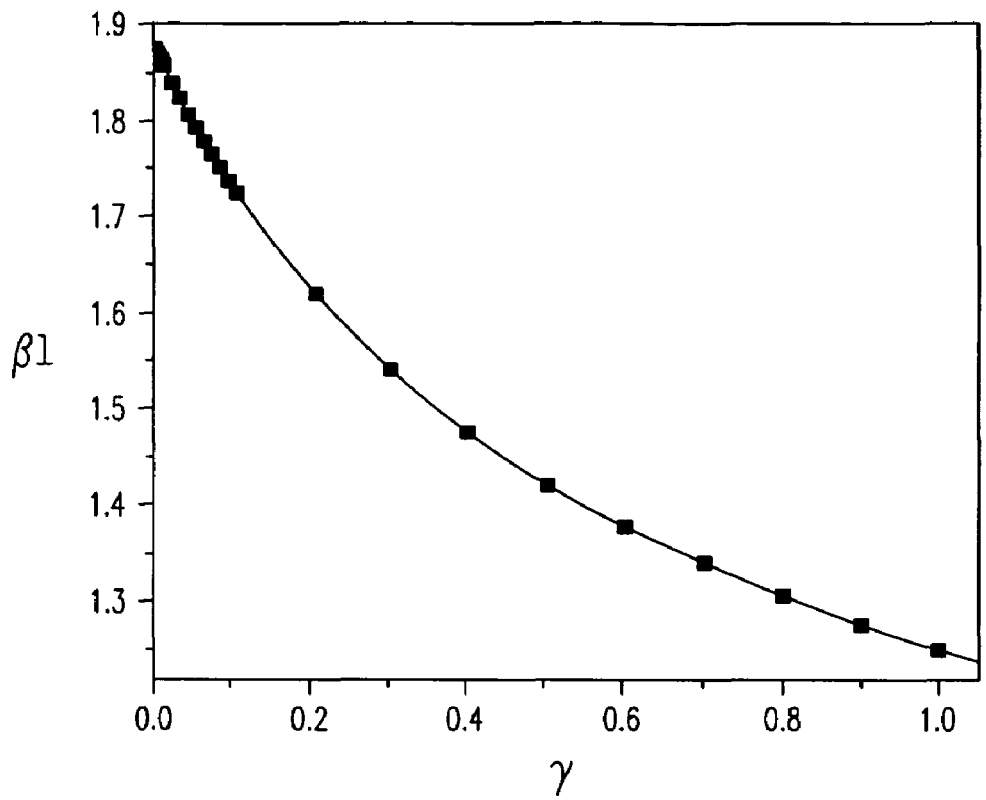
FIG. 6 is a graph illustrating a frequency response of the cantilever of FIG. 5 according to an example embodiment.

FIG. 6 shows the variation of βl with γ. For a given mass, βl was calculated using the curve fit equation and results were substituted into Eq. (11) to yield the natural frequency with the imposed mass. In the limit that γ=0, Eq. (11) reduces to that of a simple beam clamped at one end with βl=1.875 for the natural harmonic. The dashed line represents a fit of βl=1.875/(1+4γ)$^{1/4}$.

Beam with Fixed Ends and a Concentrated Mass at Midpoint

A doubly clamped beam similar to one shown in FIG. 3 is considered. For this case, the paddle region is excluded, and the beam is assumed to be of length 2l with an additional mass m located at x=l. The boundary conditions at x=0 require that both the deflection and slope be zero. From these four conditions, the following equations are generated:

$$C_2 + C_4 = 0, \quad (12)$$

$$C_1 + C_3 = 0 \quad (13)$$

resulting in $C_3 = -C_1$, $C_4 = -C_2$. The symmetry boundary condition at the middle of the beam x=l requires that the slope is zero, while the second boundary condition is similar to given by Eq. (8b):

$$C_1(\cos\eta - \cosh\eta) - C_2(\sin\eta + \sinh\eta) = 0, \quad (14)$$

$$C_1 \left[ \cos\eta + \cosh\eta - \frac{1}{2}(\gamma\eta(\sin\eta - \sinh\eta)) \right] - \\ C_2 \left[ \sin\eta - \sinh\eta + \frac{1}{2}\gamma\eta(\cos\eta - \cosh\eta) \right] = 0. \quad (15)$$

The frequency parameters β are found as solutions of frequency equation $$(\cos\eta \sin h\eta + \sin\eta \cos h\eta) - \tfrac{1}{2}\gamma\eta(1 - \cos\eta \cos h\eta) = 0. \quad (16)$$

The approximation of the resulting natural frequency based on the mode of the beam without attached mass is given by $$f_0 = 1.26 \left[ \frac{EI}{l^3(m + m_{beam})} \right]^{1/2}. \quad (17)$$

Beam with a Discontinuous Moment of Inertia

Figure 7:
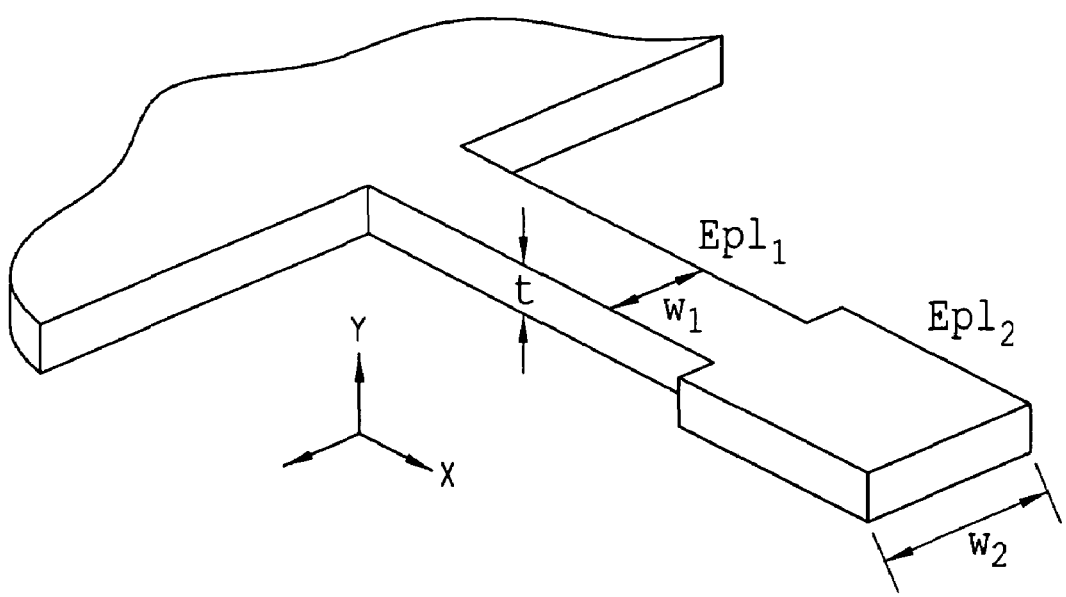
FIG. 7 is a schematic diagram of a cantilever beam with a discontinuous moment of inertia at a known distance from the clamped end of the beam according to an example embodiment.

The equation of motion is the same as before, and therefore the general solution of Eq. (4) may be used for both beam segments (see FIG. 7). For the clamped and free ends, the boundary conditions require that slope and deflection (at x=0), along with moment and shear (at x=$l_2$) be zero. The system of equations representing the boundary conditions is obtained as $$C_2 + C_4 = 0, \quad (18)$$

$$C_1 + C_3 = 0, \quad (19)$$

$$-C_1^* \sin\eta_2 - C_2^* \cos\eta_2 + C_3^* \sin h\eta_2 + C_4^* \cos h\eta_2 = 0, \quad (20)$$

$$-C_1^* \cos\eta_2 + C_2^* \sin\eta_2 + C_3^* \cos h\eta_2 + C_4^* \sin h\eta_2 = 0, \quad (21)$$

where $\eta_i = \beta_i l_i$, $\beta_i^4 = \omega^4 (\rho A_i / EI_i)$, and $A_i$ and $I_i$ define the cross-sectional area and moment of inertia, respectively, of the first (i=1) and second (i=2) beam segments.

The compatibility and equilibrium equations are satisfied at the junction of the two beam segments. Continuity at x=$l_1$ gives $$C_1(\sin\eta_1 - \sin h\eta_1) + C_2(\cos\eta_1 - \cos h\eta_1) - C_2^* - C_4^* = 0, \quad (22)$$

$$\xi[C_1(\cos\eta_1 - \cos h\eta_1) - C_2(\sin\eta_1 + \sin h\eta_1)] - C_1^* - \\ C_3^* = 0, \quad (23)$$

$$-\phi[C_1(\sin \eta_1 + \sin h\eta_1) + C_2(\cos \eta_1 + \cos h\eta_1)] + C_2^* - C_4^* = 0, \quad (24)$$

$$-\psi[C_1(\cos \eta_1 + \cos h\eta_1) - C_2(\sin \eta_1 + \sin h\eta_1)] + C_1^* C_3^* = 0, \quad (25)$$

where $\xi = \beta_1/\beta_2$, $\phi = (I_1/I_2)\xi^2$, and $\psi = (I_1/I_2)^2\xi^3$. For a beam of uniform thickness and $w_1 = 0.5\ w_2$, $\xi = 1$ $\phi = \frac{1}{2}$, and $\psi = \frac{1}{4}$.

Figure 8:
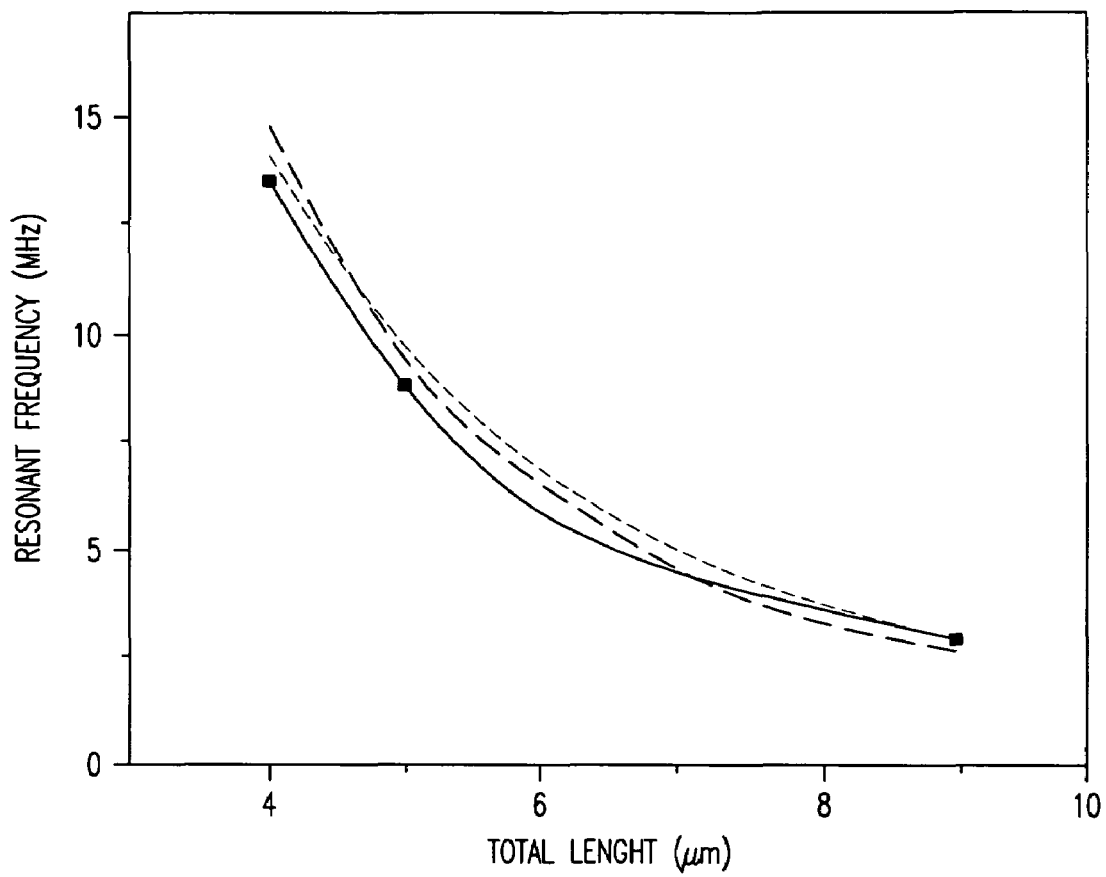
FIG. 8 is a schematic diagram of measured versus calculated resonant frequency for various cantilever beam lengths according to an example embodiment.

Considering $\eta_i$ as being small, the expansion of Eqs. (20)-(25) to order 2, yields the following matrix form:

$$\begin{bmatrix} 0 & 0 & -\kappa_2 & \lambda_- & \kappa_2 & \lambda_+ \\ 0 & 0 & \lambda_- & \kappa_2 & \lambda_+ & \kappa_2 \\ 0 & -\kappa_1^2 & 0 & -1 & 0 & -1 \\ -\xi\kappa_1^2 & 2\xi\kappa_1 & -1 & 0 & -1 & 0 \\ -2\varphi\kappa_1 & -2\varphi & 0 & 1 & 0 & -1 \\ -2\psi & 0 & 1 & 0 & -1 & 0 \end{bmatrix} \begin{bmatrix} C_1 \\ C_2 \\ C_1^* \\ C_2^* \\ C_3^* \\ C_4^* \end{bmatrix} = 0, \quad (26)$$

where $$\kappa_i = \omega^{1/2}\alpha_i,\ \lambda_\pm = \frac{1}{2}\omega\alpha_2^2 \pm 1,$$

and $\alpha_i = (\rho A_i l_i / EI_i)^{1/4}$. This equation can be solved explicitly for $\omega$, giving $$\omega_\mp = \left\{ \frac{4\alpha_1\alpha_2^3\xi\psi + 4\alpha_1^3\alpha_2\varphi + 2\alpha_1^2\alpha_2^2(\xi\varphi + \psi) \mp 2\alpha_1\alpha_2\{(2\alpha_1^2\varphi + 2\alpha_2^2\xi\psi + \alpha_1\alpha_2(\xi\varphi + \psi)]^2 - 4\alpha_1^2\alpha_2^2\varphi\psi\}}{\alpha_1^4\alpha_2^4} \right\}^{\frac{1}{2}} \quad (27)$$

where $\omega_-$ and $\omega_+$ are the resonant mode and first harmonic, respectively. FIG. 8 shows reasonable agreement between measured and calculated natural frequency for polycrystalline silicon beams with discontinuous moments of inertia. In the regime in which $l_2$ is small and $w_2$ is slightly larger than $w_1$, dynamic behavior can be described with the simple rectangular beam model. Calculations in the large $l_2$ and $w_2$ limit show a large deviation from the simplified model. In FIG. 8, the solid line represents measured resonant frequency data for various beam lengths. Calculations were obtained from Eq. (27) (dashed line) assuming a 1 μm×1 μm pad, $w_1 = 0.5\ w_2 = 0.5$ μm, $t = 160$ nm, $E_{polySi} = 179$ GPa, $\rho_{polySi} = 2300$ kg/m3, and total length=$l_1+l_2$. Calculations using the simple beam Eq. (11) (dotted line) assume a constant width $w=0.5$ μm, with $\gamma=0$ and $\beta l=1.875$.

Rotational Inertia Considerations

Figure 9:
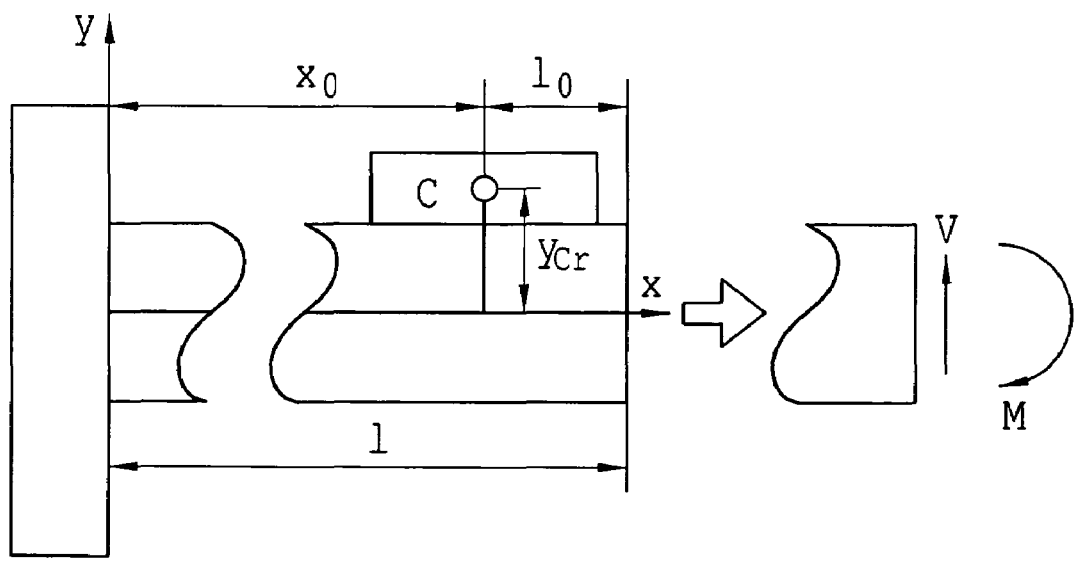
FIG. 9 is a schematic diagram of a cantilever beam with added mass at a specified distance from the clamped end of the beam according to an example embodiment.
Figure 10A:
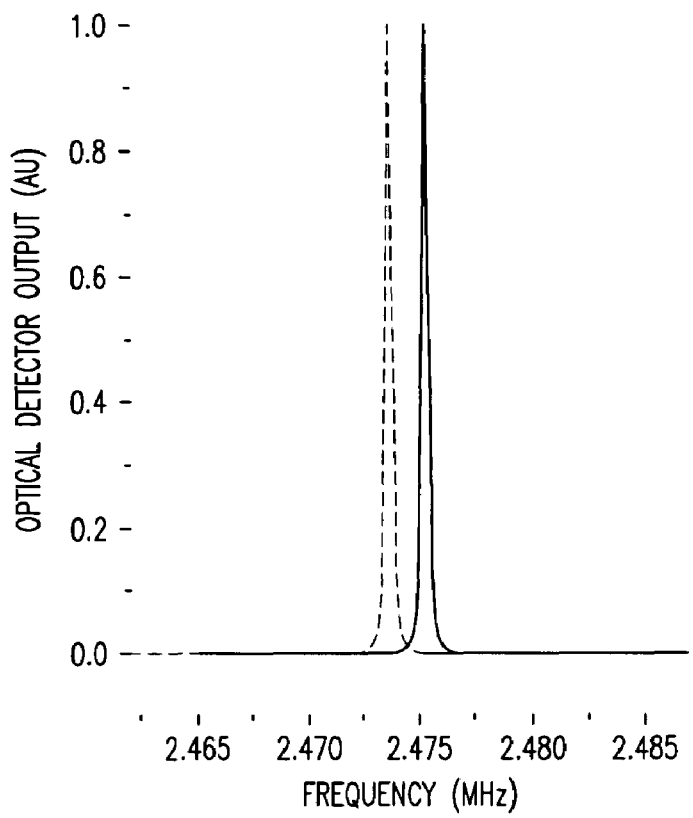
FIGS. 10A, 10B, 10C and 10D illustrate calibration frequency spectra for cantilevers with and without various diameter adsorption sites according to an example embodiment.
Figure 10B:
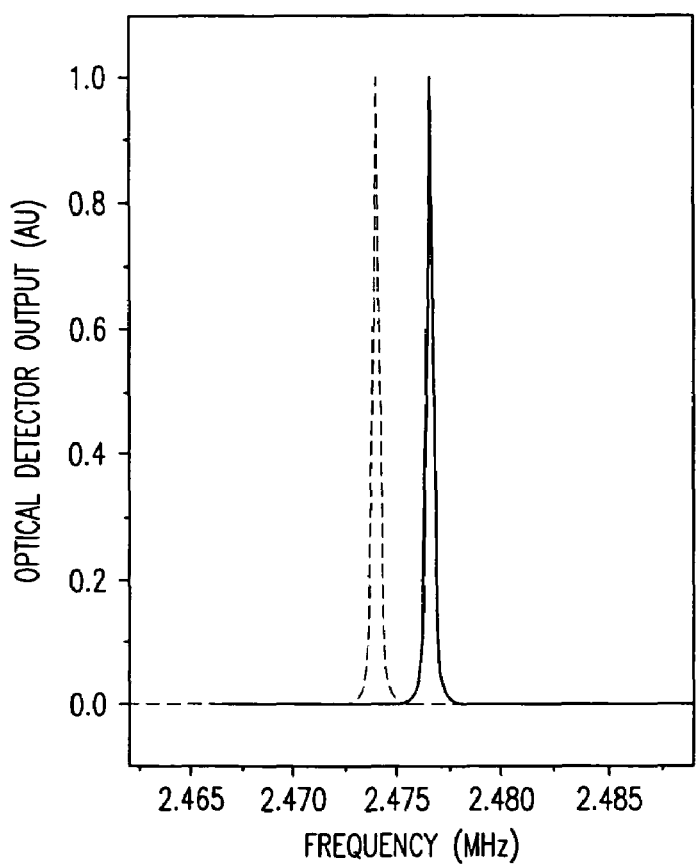
Figure 10C:
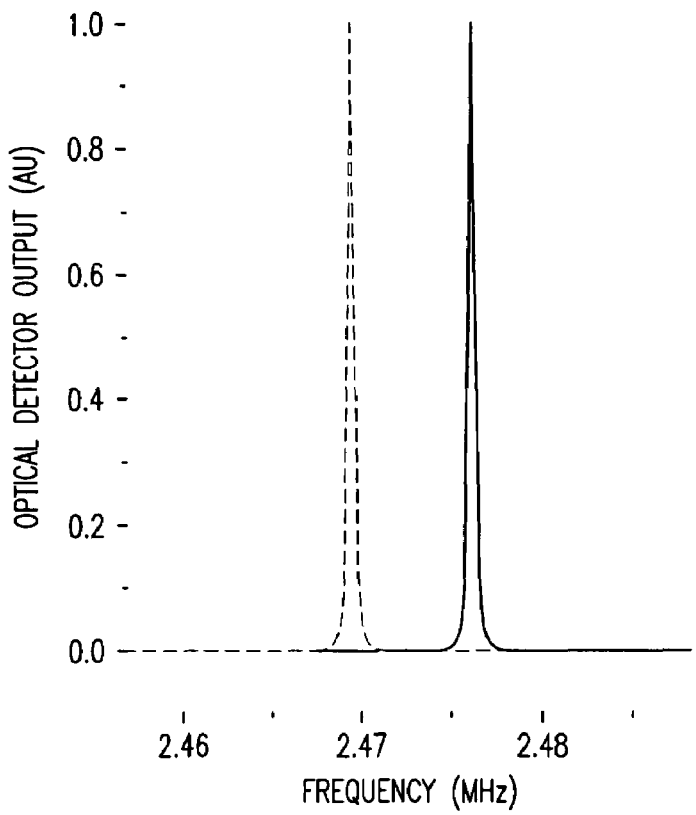
Figure 10D:
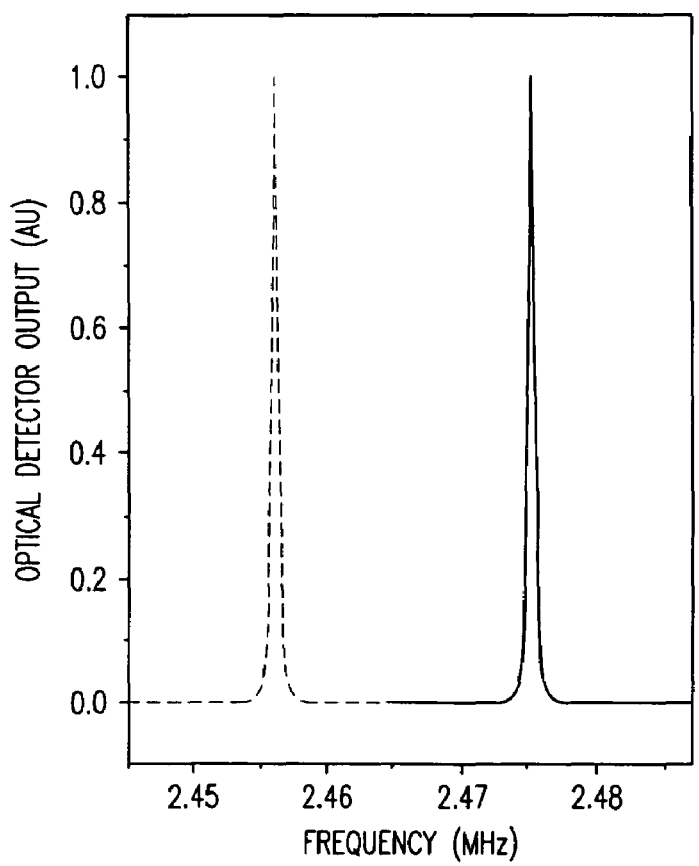

In this case, a beam with an attached mass being taken into account through boundary conditions was considered. As shown in FIG. 9, the mass is considered to be attached at the free end of the beam. Since the mass was located at $x=x_0$, an additional moment arises in the boundary condition. Only the Cr layer is shown. The rotational inertia of the added mass is taken into consideration through boundary conditions. The adopted approach allows determination of an accurate eigenfrequency of the beam. In the framework of Euler-Bernoulli, the boundary conditions at $x=0$ require that deflection and slope to vanish, and moment and shear at $x=l_0$ are formulated as follows:

$$EI\frac{\partial^2 y}{\partial x^2} = l_0(M_{Cr} + M_{Au})\frac{\partial^2 y}{\partial t^2} - \left[M_{Cr}\left(l_0^2 + y_{Cr}^2 + \frac{R^2}{4}\right) + M_{Au}\left(l_0^2 + y_{Au}^2 + \frac{R^2}{4}\right)\right]\frac{\partial^3 y}{\partial x \partial t^2}, \quad (28a)$$

$$EI\frac{\partial^2 y}{\partial x^3} = (M_{Cr} + M_{Au})\left[\frac{\partial^2 y}{\partial t^2} - l_0\frac{\partial^3 y}{\partial x \partial t^2}\right], \quad (28b)$$

where h, $h_{Cr}$, and $h_{Au}$ are the thickness of the beam, Cr layer, and Au layer, correspondingly, with $y_{Cr}=(h+h_{Cr})/2$, $y_{Au}=h_{Cr}+(h+h_{Au})/2$, and $l_0=1-x_0$. The term proportional to the radius square of the metallic dot takes into account the rotational inertia of the dot since $J=\rho h\pi R^4/4 = M\ R^2/4$. Calculations show that the influence of the rotational inertia on the frequency shift can be essential. In order to study the sensitivity of the beam frequency to the attached mass when rotational inertia is taken into account, Eq. (28) is rewritten in the following form:

$$\frac{\partial^2 \hat{y}}{\partial \hat{x}^2} = \hat{l}_0\gamma\frac{\partial^2 \hat{y}}{\partial \hat{t}^2} - \gamma(\hat{l}_0 + \hat{r}^2)\frac{\partial^3 \hat{y}}{\partial \hat{x}\partial \hat{t}^2}, \quad (29a)$$

$$\frac{\partial^3 \hat{y}}{\partial \hat{x}^3} = \gamma\frac{\partial^2 \hat{y}}{\partial \hat{t}^2} - \gamma\hat{l}_0\frac{\partial^3 \hat{y}}{\partial \hat{x}\partial \hat{t}}, \quad (29b)$$

where $\hat{l}_0 = 1 - \hat{x}_0$ and the nondimensional quantities are defined as $$\hat{y} = \frac{y}{l}, \quad (30)$$

$$\hat{x} = \frac{x}{l}, \quad (31)$$

$$\hat{t} = t\sqrt{\frac{EI}{\rho A_0 l^4}}, \quad (32)$$

$$\hat{r} = \sqrt{\frac{J}{mAl^2}}, \quad (33)$$

with $\hat{r}$ as the gyration radius.

Separation of variables and substitution of the mode shape defined by Eq. (4) into the boundary conditions leads to the following frequency equation:

$$1 + \cos\beta\cosh\beta + \gamma\beta\Big[(\cos\beta\sinh\beta - \sin\beta\cosh\beta) + \quad (34)$$
$$2\beta l'_0\sin\beta\sinh\beta - \beta^2\big(l_0'^2 + r'^2\big)(\cos\beta\sinh\beta + \sin\beta\cosh\beta)\Big] +$$
$$\gamma^2\beta^4 r'^2(1 + \cos\beta\cos\beta\cosh\beta) = 0$$

The perturbation procedure with the nondimensional mass $\gamma \ll 1$ considered as a small parameter is implemented. By placing $\beta = \beta_0 + \gamma\beta_1$ and directly substituting into the frequency Eq. (34) while limiting the expansion by terms linear in $\gamma$, the following expression for the frequency parameter is obtained:

$$\beta = \beta_0\{1 - \gamma[1 + 2\beta_0 l_0 g_1(\beta_0) + \beta_0^2(l_0^2 + r'^2)g_2(\beta_0)]\}, \quad (35)$$

where $$g_1 = \frac{\sin\beta_0(1-\Gamma_1)}{\Gamma_2 + \Gamma_3\Gamma_4} = -0.734, \quad (36)$$

and $$g_2 = \frac{\Gamma_3 + \Gamma_2\Gamma_4}{\Gamma_2 + \Gamma_3\Gamma_4} = 0.539, \quad (37)$$

where $$\Gamma_1 = \sin h2\beta_0 + \cos h2\beta_0, \quad (38)$$

$$\Gamma_2 = \sin\beta_0 + \cos\beta_0, \quad (39)$$

$$\Gamma_3 = \sin\beta_0 - \cos\beta_0, \quad (40)$$

$$\Gamma_4 = \sin h2\beta_0 + \cos h2\beta_0, \quad (41)$$

with $\beta_0 = 1.875$ as the solution of the unperturbed frequency equation for the cantilever (i.e., $1 + \cos\beta_0 \cos h \beta_0 = 0$).

Arrays of cantilevers with eigenfrequencies from 1 to 15 MHz with integrated Au dots of varying size were fabricated using the process flow described earlier and shown in FIG. 1A-1F. In addition to the clamped-free oscillators, clamped-clamped versions were fabricated for comparative purposes. To test the sensitivity of the oscillator arrays, baseline measurements of the natural frequency were obtained in vacuum. Each array included reference oscillators; that is, devices without Au contacts. The Au was then removed and shift in the resonant frequency due to the etched Au mass was observed. Measured frequency spectra for 10-μm-long cantilevers before (dashed line) and after (solid line) the removal of the Au dots is shown in FIGS. 10A, 10B, 10C and 10D. The Au dots are respectively of diameters 50, 100, 200 and 400 nms in FIGS. 10A-D. Reference cantilevers showed no shift in the frequency. These results suggest an absence of nonspecific etching or adsorption during the aqueous Au etch. For these devices, the mechanical quality factor (Q), defined as the ratio of the resonant frequency to the full width at half-maximum of the spectral response, remained at a constant value of 8500 during the control experiments. The lack of dependence of Q on $m_{Au}$ indicates the absence of appreciable surface-dominated dissipation mechanisms due to additional mass loading of the Au dots.

Figure 11:
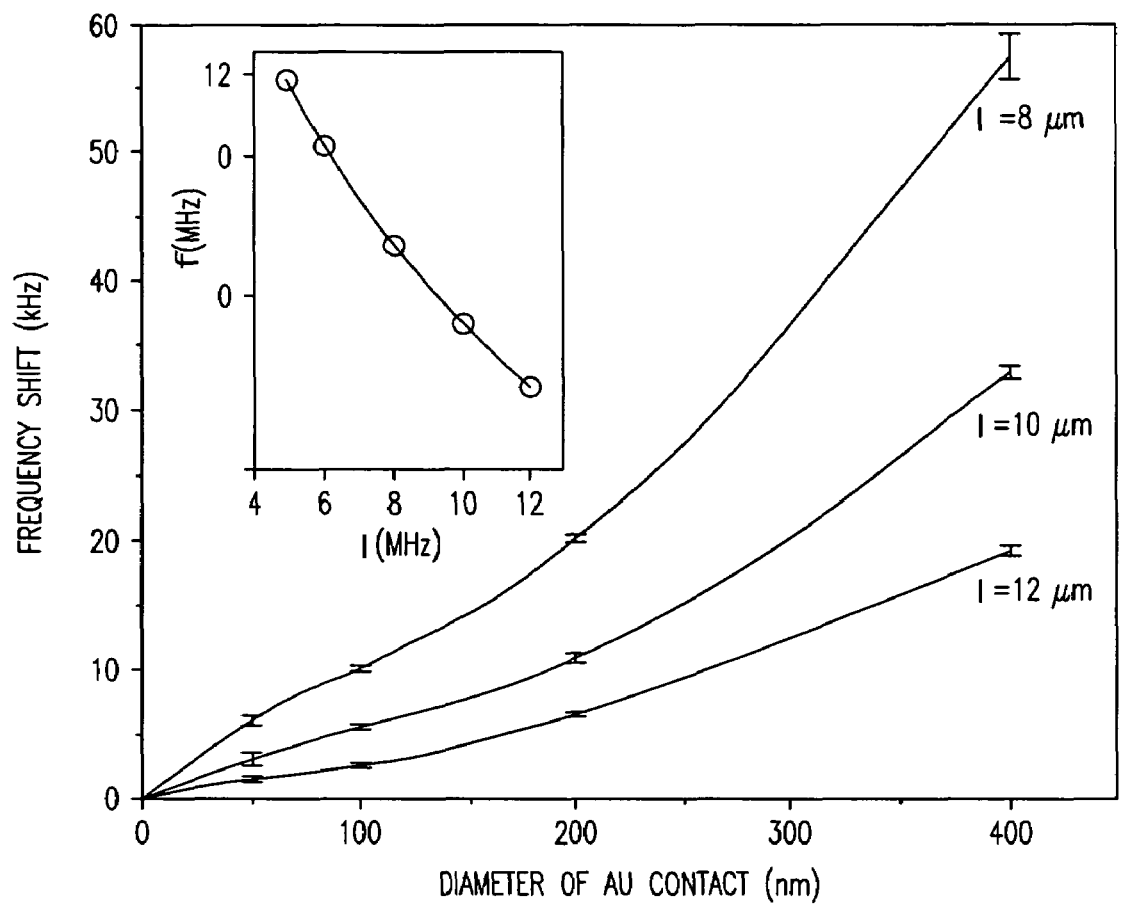
FIG. 11 is a calibration plot of frequency versus adsorption site diameter according to an example embodiment.

FIG. 11 represents calibration measurements indicating a frequency-mass loading dependence of cantilevers with varying length. It shows detailed normalized frequency shift data for three different length cantilevers. The inset shows natural frequency variations with the length of the rectangular cantilevers. Device dimensions were w=1 μm and t=250 nm with Au thickness of 15 nm. The analytic fit appears slightly larger than the measured values. The discrepancy is due to the oversimplified assumption regarding the cantilever beam with a concentrated mass at the free end, which assumes mass loading is located at the very end of the oscillator. Additionally, the model does not account for pinholes as well as impurity defects in the deposited gold layer. For these devices with Q=8500, we estimate 2.7, 5.7, and 11.3 attograms (ag) as the minimum resolvable mass for the l=8, 10, and 12 μm cantilevers, respectively.

Figure 12A:
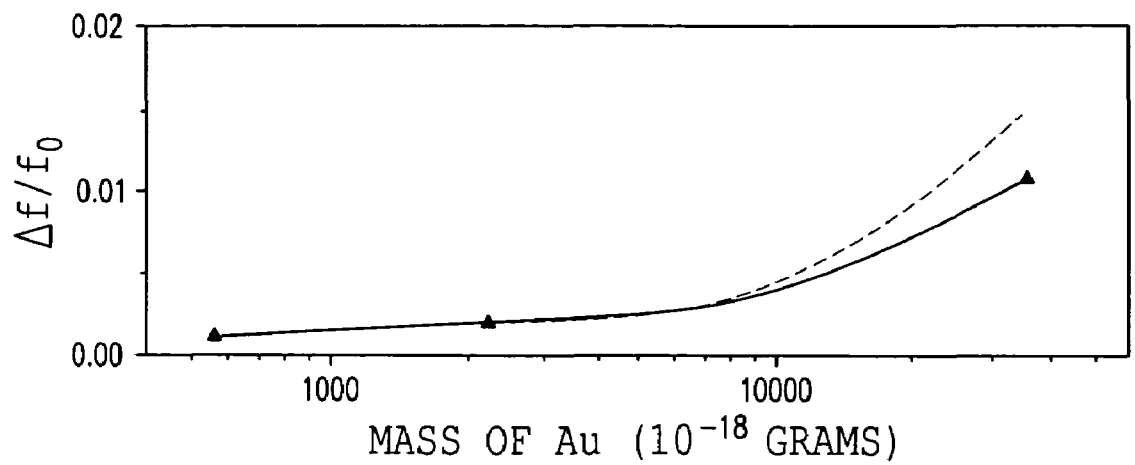
FIGS. 12A, 12B and 12C are plots of measured normalized frequency shift versus adsorption site mass for various length cantilevers according to an example embodiment.
Figure 12B:
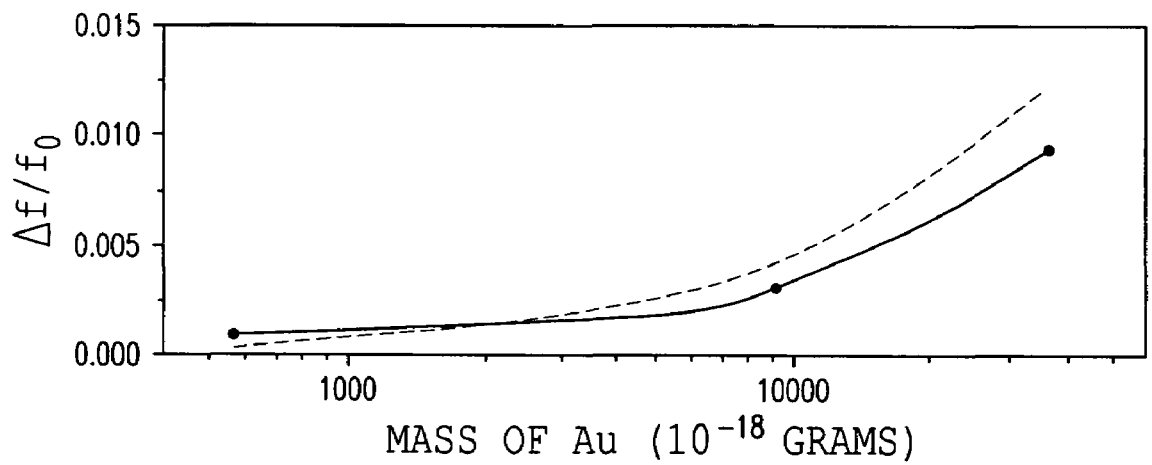
Figure 12C:
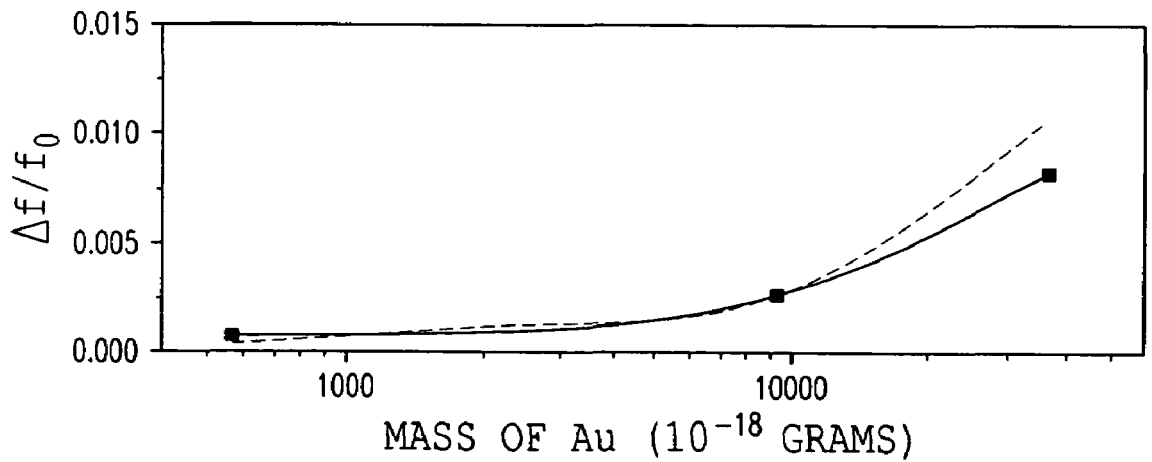

FIGS. 12A, 12B and 12C are plots of measured normalized frequency shift (solid line) versus mass of Au contact for 8, 10 and 12 μm long cantilevers respectively. The dashed lines represent a fit generated from Eq. (11).

Figure 13:
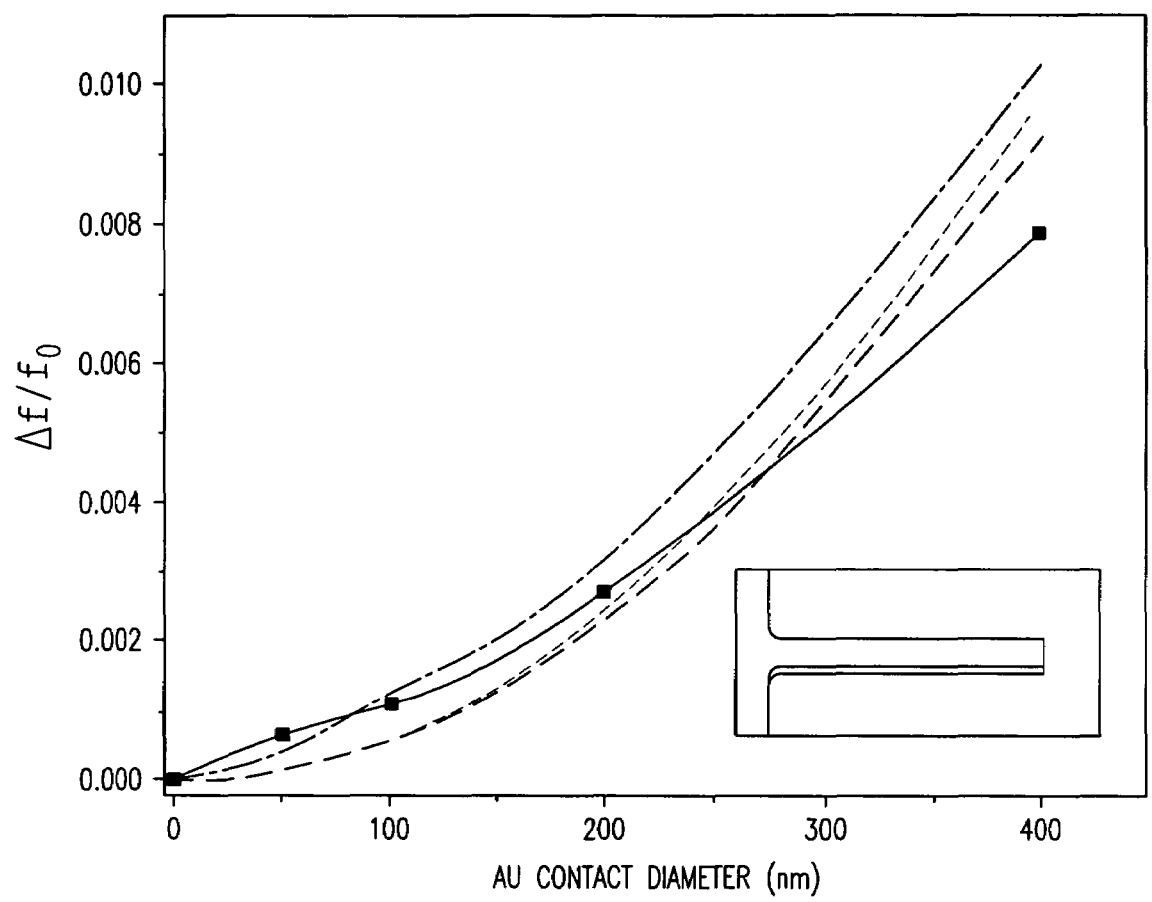
FIG. 13 is a plot illustrating measured and calculated normalized frequency shift dependence on additional mass loading on a cantilever beam shown in an inset according to an example embodiment.

Comparison of the measured and calculated normalized frequency shift plots as a function of the Au contact diameter is shown in FIG. 13. Calculations of the simplified model were performed using analysis of a cantilever beam with a concentrated mass at the free end. A better approximation may be achieved by accounting for the exact location of the added mass, taking rotational inertia considerations into account. Both models show significant quantitative success; however, they clearly have some substantial limitations. In each case, particle properties of the contact are neglected; for example, there is no consideration of the exact topography of the particle. For a complete theoretical treatment, effects such as microstructural defects, grain morphology, and impurities may need to be considered.

Analytical models described earlier are based on Euler-Bernoulli beam theory and neglect rotational inertia of the beam and shear deformation. In order to verify the analytic models, the frequencies of the beam were calculated using a finite element method (FEM). A three-dimensional model was built based on the quadratic 20 node brick element. Material properties of polycrystalline silicon used for the calculations are E=179 GPa, ρ=2300 kg/m³, and ν=0.28. Densities of Cr and Au are $\rho_{Cr}$=7140 kg/m³ and $\rho_{Au}$=19300 kg/m³, correspondingly. The length of the beam was subdivided into 160 elements, while the thickness and the half-width was subdivided into four elements. The study of convergence was performed in order to ensure the relative error in the first frequency less than $10^{-4}$. FIG. 13 further shows that when rotational inertia is considered, the results agree well with the FEM simulation. FIG. 13 illustrates a comparison of measured (solid line) and calculated normalized frequency shift dependence on the additional mass loading of a 10-μm long, 1-μm wide, and 250-nm thick clamped-free beam resonator shown in the inset. Three different calculated frequency shift traces correspond to the simple model Eq. (11) (dash-dot line), taking account of the mass location (dotted line), and both rotational inertia consideration and finite element analysis (dashed line).

The first rotational inertia correction is on the order of $\gamma l_0$ and takes into acount the fact that the mass is attached at $x=x_0$. The second rotational inertia correction term, which takes into account the rotational inertia of the mass around its central axis, is on the order of $\gamma l_0^2$ [see Eq. (35)]. Since $g_1$ is negative, this term decreases the frequency shift as we observed in our results. The influence of the rotational inertia of the mass attached to the beam can be essential and produce a discrepancy of about 10% in the frequency shift.

Figure 14A:
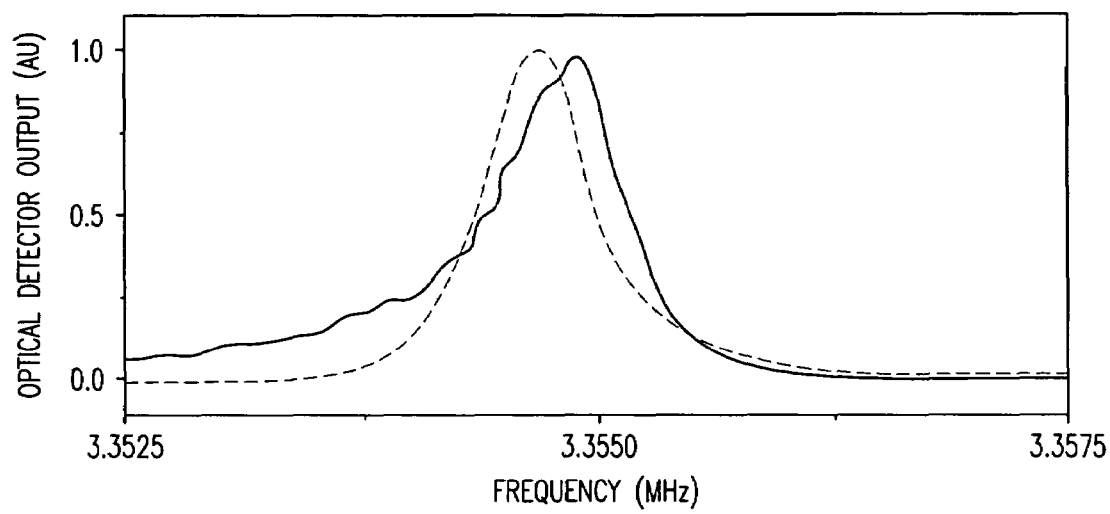
FIGS. 14A and 14B are plots illustrating measured shift in resonant frequency spectra before and after different size self-assembled thiolate areas on a cantilever beam according to an example embodiment.
Figure 14B:
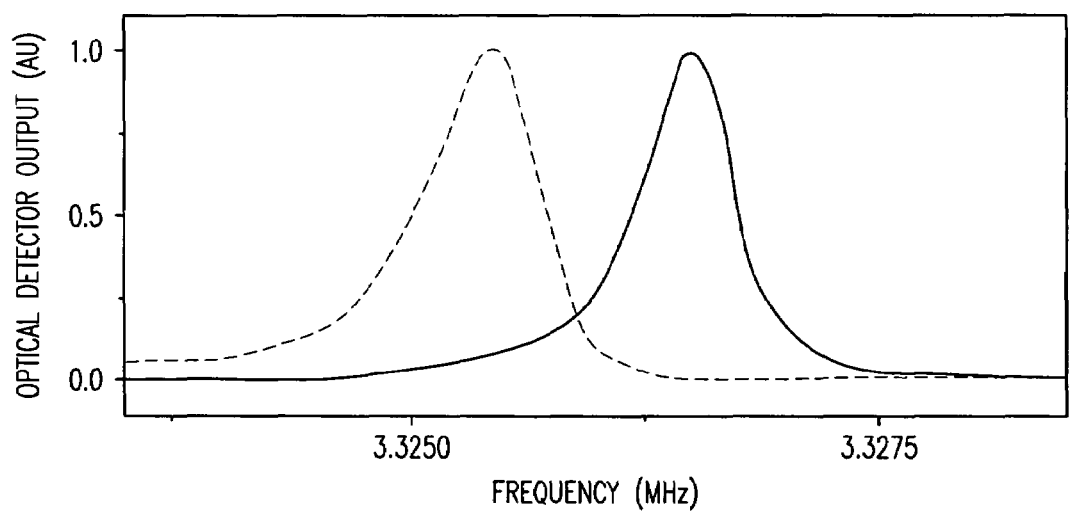

To probe the amount of thiolate binding to the Au contacts, the frequency spectra were measured before (solid line) and after (dashed line) the thiolate self-assembly. FIGS. 14A and 14B show the measured shift in the resonant frequency for DNP-PEG4-C11 thiol binding on 50- and 400-nm-diam Au contacts respectively. The measured frequency shifts were 125 Hz and 1.10 kHz, corresponding to calculated masses of 6.3 and 213.1 ag, respectively.

Figure 15A:
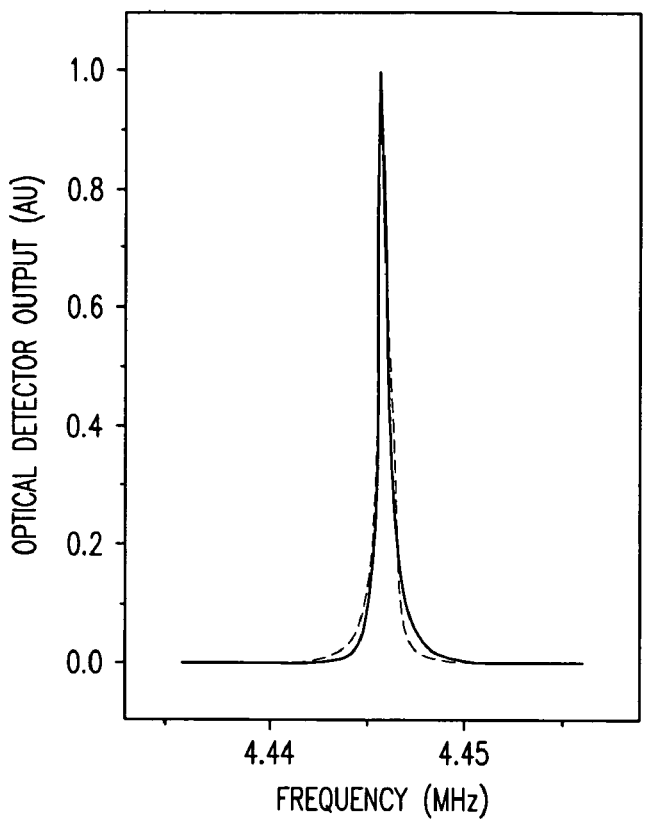
FIGS. 15A, 15B and 15C are plots illustrating frequency spectra of various paddle shaped oscillators according to an example embodiment.
Figure 15B:
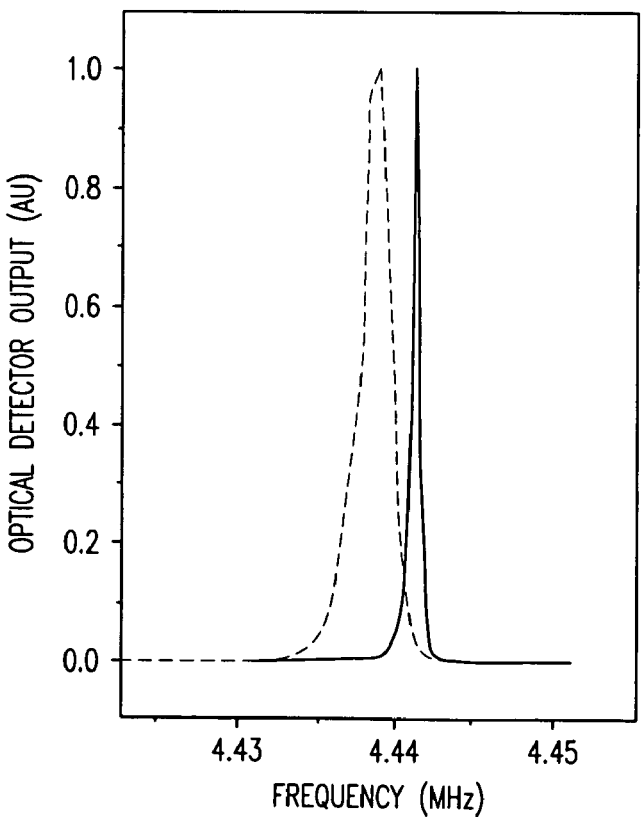
Figure 15C:
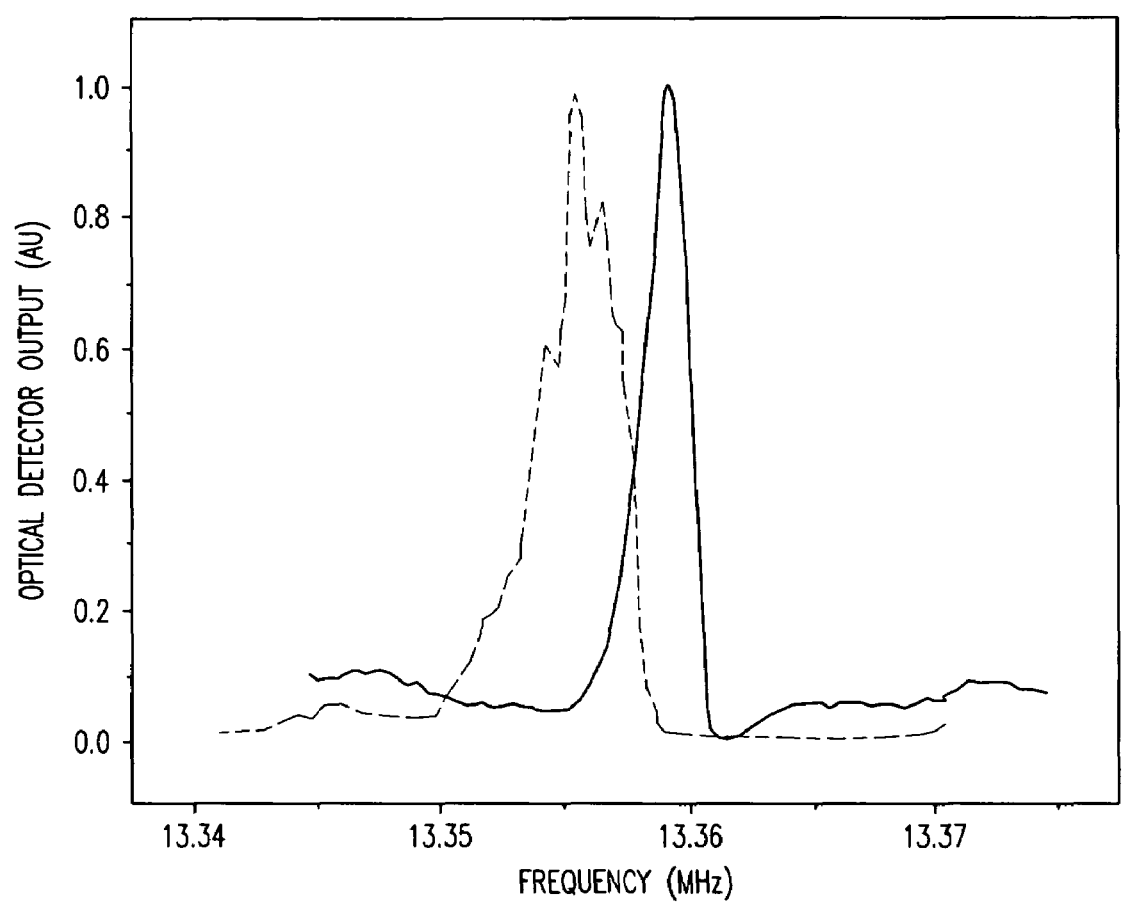

To further enhance the sensitivity, measurements were performed using paddle oscillators of various lengths, of 0.5 mm width, and with a 1 μm×1 μm square paddle located at the free end of the beam. Control measurements of 6-μm-long paddle oscillators consistently show a lack of a frequency shift, which signifies an absence of nonspecific binding of thiolate molecules as shown in FIG. 15A. This is consistent with the control experiments performed on bulk substrates. FIG. 15B shows a 1.5 kHz shift in the frequency for the same size oscillator with a 150-nm-diam Au contact. For a 4-μm-long paddle oscillator, the measured frequency shift was 3.53 kHz as shown in FIG. 15C. The calculated frequency shifts were 1.14 and 3.01 kHz, respectively. From the measured frequency shifts at a given quality factor, we estimate the smallest resolvable mass of 0.79 and 0.39 ag for the 6-, and 4-μm-long paddle oscillators, correspondingly. Other cantilever dimensions include t=160 nm and w=0.5 μm with a 1 μm×1 μm paddle.

200-nm-wide, doubly clamped paddle oscillators of various lengths, with 1 μm×1 μm paddles have been fabricated and tested. In contrast to cantilever-type oscillators, where release-related stiction could potentially occur during sacrificial layer removal, doubly clamped devices uniquely offer a wide range of flexibility in the creation of low-mass, large surface-to-area microstructures. Because of strong liquid capillary forces during release, the free end of a low-stiffness cantilever may permanently adhere to the substrate. This problem can be circumvented through either supercritical drying or passivation with a lubricating layer. However, in either case, contamination involving foreign particulates and additional surface layers can potentially enhance dissipation and degrade sensitivity. Stiction of beams has been observed where w<500 nm and l>15 μm. On the other hand, low-stress clamped-clamped beams have been fabricated with w=200 nm and l>30 μm. These devices can offer comparable mass sensitivity, however, the additional boundary condition degrades the mechanical quality factor through clamping losses into the substrate. The measured devices had a Q factor of about 4500.

Figure 16A:
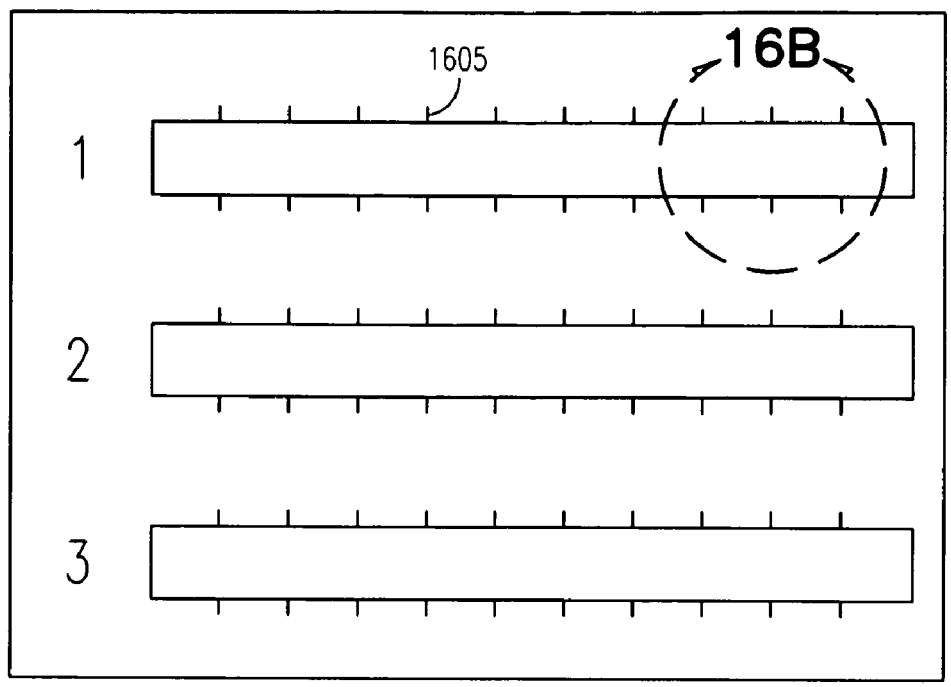
FIGS. 16A, 16B, 16C and 16D illustrate various cantilevers formed according to an example embodiment.
Figure 16B:
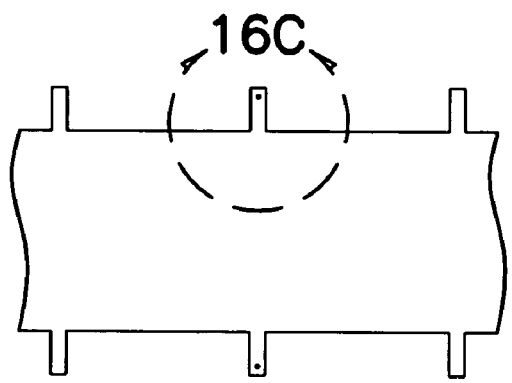
Figure 16C:
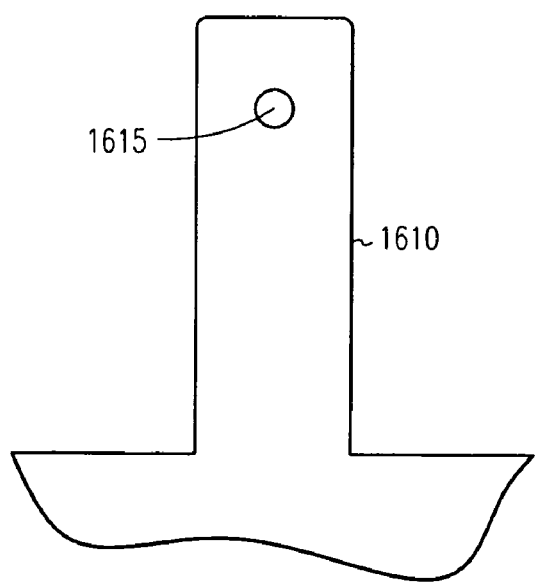
Figure 16D:
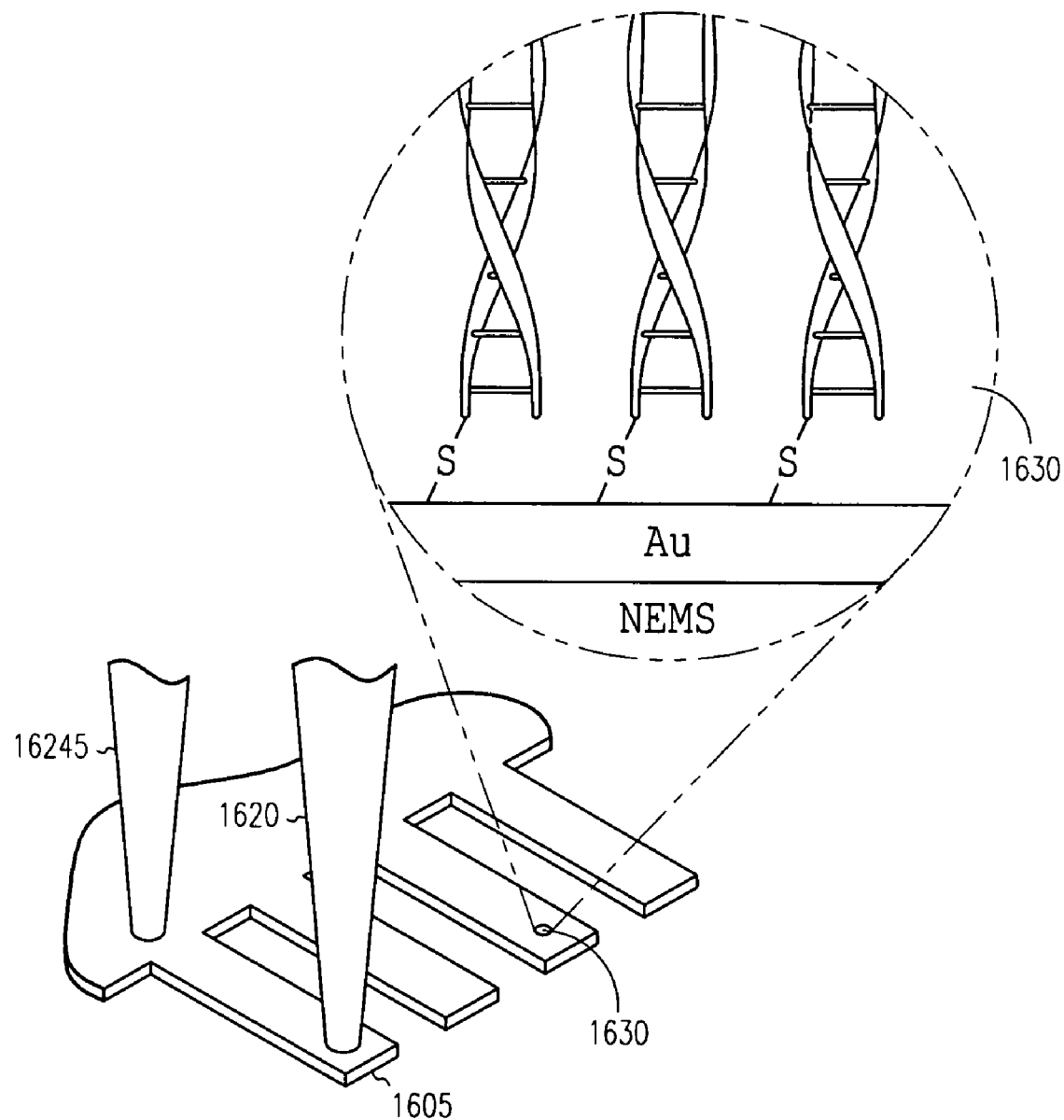

A further example embodiment is shown in FIGS. 16A, 16B, 16C and 16D. FIG. 16A shows arrays of cantilevers 1605 of varying lengths. Cantilevers 1605 of lengths l=3.5 μm, l=4.0 μm, and l=5.0 μm are shown in FIG. 16B. A perspective view of a 90 nm thick silicon nitride cantilever 1610 with a 40 nm circular Au aperture 1615 centered 300 nm away from the free end is show in FIG. 16C. FIG. 16D is a schematic of an optical measurement setup displaying arrays of cantilevers 1605 with and without Au dots 1615, as well as a red HeNe laser 1620 and a driving, blue, 415 nm diode laser 1625 at the free end and near the periphery of the clamped end respectively. Inset schematic 1630 illustrates the binding strategy of the thiolated double stranded DNA molecules to the Au dots near the free end of the cantilevers 1605.

In one example embodiment, the binding of functionalized 1578 base pair long double-stranded deoxyribonucleic acid (dsDNA) molecules to nanomechanical oscillators may be detected by measuring the resonant frequency shift due to the added mass of the bound molecules. The binding of a single DNA molecule may readily be detected. The resonant frequency of individual oscillators in an array of resonator devices may be measured by thermo-optically driving the individual devices and detecting their motion by optical interference. The number of bound molecules on each device may be quantified as proportional to the measured frequency shift with a proportionality constant determined experimentally and verified by modeling of the mechanical response of the system. For the smallest and most sensitive cantilevers in one example, the mass sensitivity was 194 Hz/attogram.

The resonant frequency shift of the oscillators can be measured with high accuracy, having a practical experimental uncertainty of ~10 Hz corresponding to ~0.05 ag. The non-specific binding of material to the oscillator throughout the process, however, may limit the quantification of the specifically bound compounds for a particular analytical process. In one embodiment, measured effects of non-specific binding of material other than the DNA from solutions was approximately 0.43±0.23 ag for an oscillator of length l=3.5 μm, with 0.23 ag therefore being the approximate limiting mass resolution resulting from uncontrolled binding to the surface in our particular process. For the smallest (l=3.5 μm), most sensitive oscillator this mass uncertainty corresponds to the mass of ~0.26 DNA molecules, enabling resolution of a single molecule. With the most sensitive devices and dilute DNA concentrations, a single dsDNA molecule may be detected.

Devices may be fabricated from 90 nm thick low-pressure chemical vapor deposited low-stress silicon nitride in conjunction with a thermally grown sacrificial silicon dioxide layer. High-resolution electron beam lithography (EBL using a 100 keV JEOL JBX-9300FS), using a bi-level poly-methyl methacrylate (PMMA) resist, may be used to define the body of the cantilever oscillator. Each sample may contain arrays of oscillators. 30 nm of chromium may subsequently deposited using electron beam evaporation and lifted-off in a solution of methylene chloride. Silicon nitride may then be etched in a $CF_4$ plasma using Cr as an etch mask. The Cr may then be removed using wet chemical etching and a subsequent $O_2$ plasma etching. A second, registered, EBL level using a bi-layer PMMA resist may be performed to define circular openings near the free end of the cantilevers, where the Au dots were to be located. Within each sample, a portion of the fabricated NEMS array may be reserved for the evaluation of the selectivity of the binding events, and hence here, Au dots were not defined. Electron beam evaporation of 5 nm of Cr and 15 nm of Au and subsequent lift-off was carried out to define the binding sites. Devices were then released in hydrofluoric acid, rinsed in de-ionized water and dried in flowing nitrogen. FIGS. 16A-C show arrays of released oscillators with 40 nm diameter gold contacts.

One factor that may strongly affect the resonant frequency shift is the position on the surface of the oscillator where the binding takes place. Controlling the binding location may be important for creating devices with a calibrated response to the binding of individual molecules. The maximization in mass sensitivity is achieved through placement of a biomolecular-tethering site at the point where the oscillator's vibrational amplitude may be maximum. For a cantilever oscillator, maximum sensitivity may be achieved at the free end for the fundamental mode of vibration. To localize the binding site, oscillators may be formed with nanoscale gold dots at precise locations on the cantilevers to act as spatially and chemically discriminant binding sites to selectively capture disulfide modified dsDNA molecules. Because the bound dsDNA molecule is tethered to the gold nanodot at only one end, the possible frequency shift variation due to drying in the worst case configurations of the molecules all stretched toward the support end versus stretched in the opposite direction on the cantilever. While a possibly measurable effect, this has no impact on the counting of a few bound molecules. In further embodiment, materials other than gold may be used to form spatially and chemically discriminant binding sites to selectively capture desired substances.

Both excitation and detection of cantilever motion was performed by scanning laser beams, not requiring precise focusing or alignment with the oscillators. The oscillators therefore can be made much smaller than either the spot size or alignment accuracy of the lasers. The oscillator spacing should be greater than the alignment accuracy and spot size of the detection beam.

In one example, measurements were performed with the oscillators in a vacuum chamber that was evacuated to $\sim 3 \times 10^{-7}$ Torr. The out-of-plane motion of the resonators was determined interferrometrically by measuring the reflectance variation from a He—Ne laser focused at the free end of the cantilever beam. Reflection from the moving cantilever and the underlying silicon substrate set up a Fabry-Perot cavity. Device motion therefore varied the intensity of the light. Translational stages were used for adjusting the focus and position of the laser beam. The 4 µm laser spot completely covered the nanomechanical oscillator. A spectrum analyzer was used to acquire the modulated output from a photodiode to provide the frequency spectrum of the mechanical response, from which the resonant frequency could be readily extracted.

In the measurement of the resonant devices a scanning optical-thermo-mechanical motion excitation method may be used. A chopped laser beam was focused on the surface near the cantilever (FIG. 16D). At the resonant frequency of the oscillator, thermal waves produced by an intensity modulated 415 nm diode laser excite the motion of the cantilever. The dynamics of the heat transport process can be qualitatively described as injected thermal energy being carried to the system causing amplified mechanical vibrations.

The location of the driving beam is not critical, and detectable motion could be excited with displacements approaching 50 µm from the cantilever in one embodiment. The exciting beam may be scanned without critical alignment to activate each cantilever and the mechanical response measured with a second laser. In one embodiment, careful consideration to possible thermal effects or nonlinearities influencing the resonant frequency or frequency stability may be considered to definitively associate frequency shifts with bound mass. With optical drive power signals ($P_d$) less than 14 µW, positioning of the driving laser beam around the periphery of the oscillators clamped end does not appear to influence the natural frequency of the nanomechanical device. The onset of non-linearities may be seen at $P_d > 140$ µW and appears similar to the behavior previously observed using electrostatic actuation of NEMS devices. With $P_d < 14$ µW reproducible measurements of the resonant frequency may be achieved with frequency stability of about 10 Hz.

In one embodiment, the driving beam may be placed in close proximity of the clamped end and out of plane vibrations may be monitored over time. These measurements revealed a similar frequency stability of ~10 Hz over a period of 2 hrs. Similar experiments performed in the moderate nonlinear excitation regime showed chaotic resonant behavior and contact phenomenon. At even higher driving levels, devices may be ultimately immobilized through stiction, where the oscillator became attached to the underlying substrate. A photon induced drive with $P_d < 14$ µW provides an attractive actuation scheme within which thermal effects do not appear to induce resonant frequency drift.

In one embodiment, a dsDNA with 5' thiol modification may be used as a model molecular system. A 1587 bp long target dsDNA was produced through polymerase chain reaction (PCR master mix from Brinkmann, Wesyburg, N.Y.). The template used for the production of target dsDNA by PCR was a plasmid vector pVAX1/lacZ (Invitrogen, Carlsbad, Calif.). The 5' disulfide-modified forward primer used was R—S—S-GGGAGGATTGGGAAGACAATAGCA with the reverse primer being AGCAGCCACTGGTAACAG-GATTAG (Integrated DNA Technologies, Coralville, Iowa). Following the reaction, the primers and the enzyme were removed with a PCR purification kit (Qiagen Inc, Valencia, Calif.). The resulting PCR dsDNA product with one disulfide modified end was then reduced using dithiothreitol immobilized acrylamide resin ("reductacryl", Calniochem. Inc.). The reduction reaction was performed at room temperature for 15 min with agitation. Reduction resin was then removed by centrifugation. The resulting thiol-modified DNA was used immediately following reduction reaction. The target DNA was immobilized onto gold dots as shown in FIG. 16D on the cantilever surface by incubation of 5 ng/µl thiolated dsDNA in 0.1M NaCl, 10 mM sodium phosphate buffer (pH 7.4) with the cantilever surface at room temperature for two hours. Later in order to reduce the number of immobilized DNA molecules, we used diluted (0.05 ng/µl) thiolated dsDNA with a 15 minute incubation period. After immobilization, loosely bound dsDNA molecules on the surface of the devices were removed by washing the entire chip with de-ionized water. The samples were then dried with a stream of high purity nitrogen and placed into the vacuum chamber. The resulting frequency spectra were then correlated to the number of immobilized thiolated dsDNA molecules ($N_{DNA}$).

Systematic binding experiments were carried out on more than 100 nanomechanical resonators of varying dimensions. After cantilever array fabrication, initial base-line resonant frequency measurements were made for each oscillator in the array. After binding of the dsDNA, the frequency response of the individual oscillators was measured again. The frequency shift was obtained by fitting a Lorentzian function to the measured data and correlated to the known mass of a single dsDNA molecule ($m_{DNA}$=999 kDaltons). Calculations provide a magnitude of the sensitivity of 194, 109 and 54 Hz/ag for cantilevers of l=3.5, 4 and 5 µm respectively. Furthermore, calculations take into account the mass location while neglecting the rotational inertia of the attached mass. Verification of the Euler-Bernoulli model was carried out using finite element methods (FEM). Comparison of the results produced by the analytical beam model and the three dimensional FEM show good agreement.

Figure 17A:
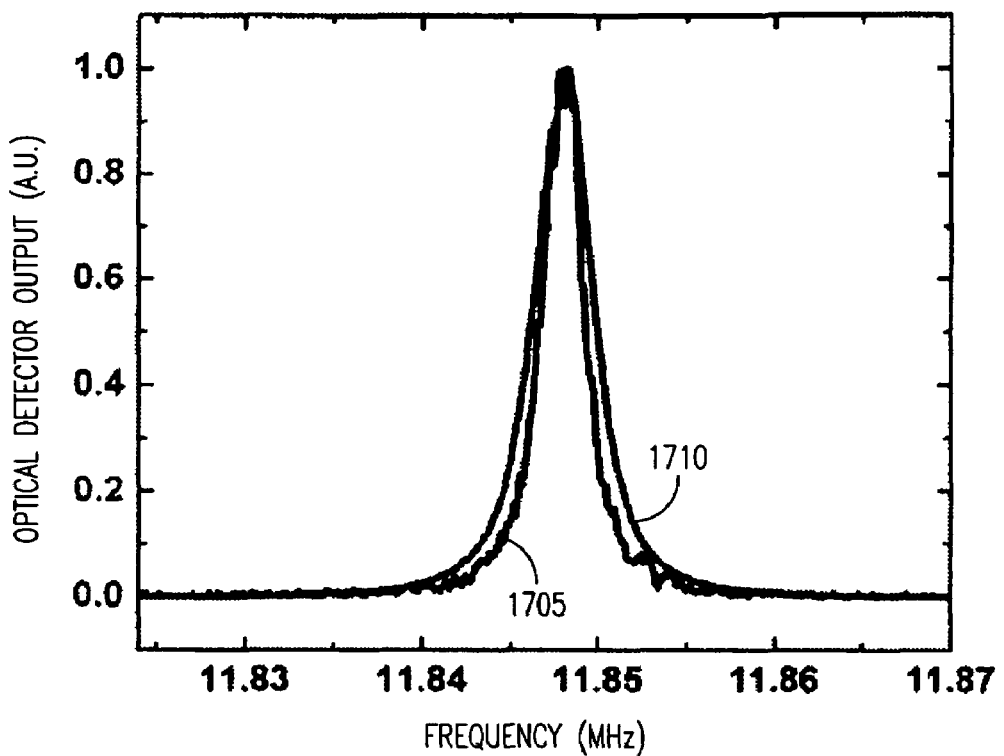
FIGS. 17A and 17B are plots illustrating frequency spectra of oscillators according to an example embodiment.

Control experiments were performed to measure non-specific binding of material from the buffer solution to the silicon nitride oscillator. For these experiments, the devices were submerged for 2 hours in a buffer solution that did not contain DNA molecules. Each device set was composed of arrays of NEMS devices comprised of cantilevers both with and without gold dots. Following the immersion, the devices were thoroughly rinsed in de-ionized water and dried with pressurized nitrogen. The devices were then measured in the fashion described above. The measured frequency shift revealed the degree of non-specific binding and its variation between oscillators of different dimensions. FIG. 17A is a characteristic spectra showing a minute change in the natural frequency corresponding to a shift resulting from nonspecific binding of the buffer solution. These characteristic features were reproducible in different sample runs for varying oscillator dimensions. From the specificity experiments, the amount of observed non-specific binding was $0.26 \pm 0.14$ $m_{DNA}$, $0.44 \pm 0.12$ $m_{DNA}$, and $0.42 \pm 0.09$ $m_{DNA}$ for cantilevers of l=3.5, 4 and 5 µm. We have also found that these frequency shifts due to the nonspecific interaction from the control buffer were independent of the presence of the gold dot.

Figure 17B:
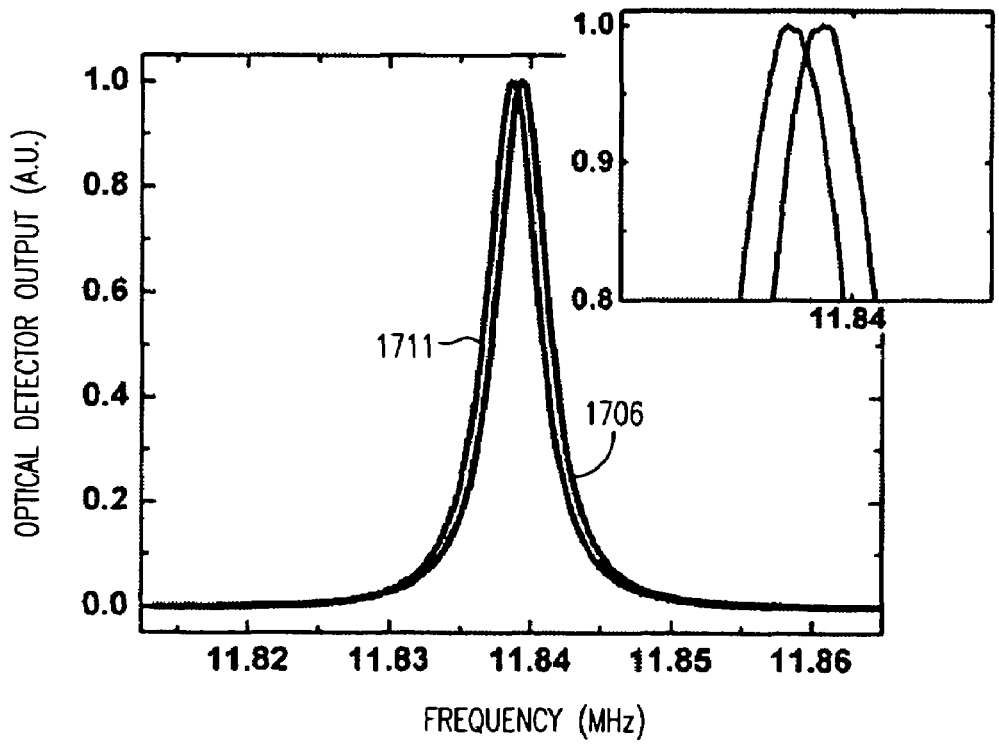

Following control experiments, new devices were immobilized with dsDNA and measured under vacuum. FIG. 17B shows characteristic DNA binding spectra indicating an easily resolvable frequency shift corresponding to the mass of 2.04 DNA molecules. During each experiment, binding selectivity of the thiolated DNA to gold was confirmed by measuring the binding response of the functionalized dsDNA cantilevers without gold dots. In our experiments, only cantilevers with gold dots displayed a frequency shift significantly greater than those due to non-specific binding. NEMS oscillators without Au dots showed a frequency shift of a similar magnitude as seen during control experiments. This lack of binding dependence to devices without gold contacts corroborates excellent binding selectivity of the thiolated dsDNA to the gold nanodots.

Frequency spectra of l=3.5 μm oscillators before 1705, 1706 and after 1710, 1711 the various stages of binding developed in this study are illustrated in FIGS. 17A and 17B. FIG. 17A illustrates a control experiment showing a frequency shift corresponding to 0.3 $m_{DNA}$. FIG. 17B illustrates a measured frequency spectra resulting from a binding event of ~2.04 DNA molecules. The mechanical quality factor (Q) of these devices ranged from 3000-5000.

Figure 18:
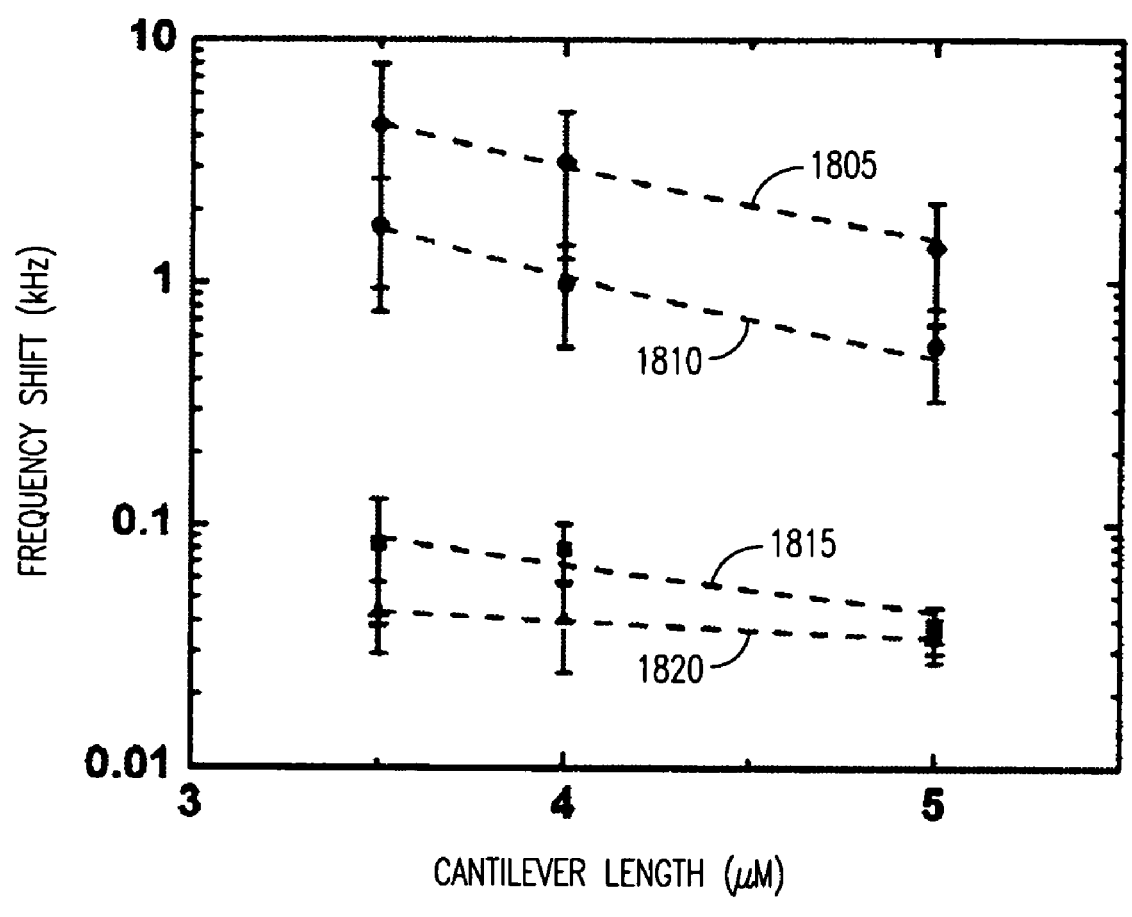
FIG. 18 is a plot of frequency shift for various cantilever lengths according to an example embodiment.

FIG. 18 shows Frequency shift with cantilever length for DNA concentrations of 0.05 ng/μl 1810 and 5.0 ng/μl 1805, and control experiments without Au dots 1815 and buffer solution without DNA 1820. The error bars indicate the standard deviation in the data. Theoretical predictions from FEM simulations show a worse case scenario of about 15% frequency discrepancy when assuming the DNA molecule perfectly stretched from the Au dot. This probably reflects the continuity of the data when measuring many molecules.

Figure 19A:
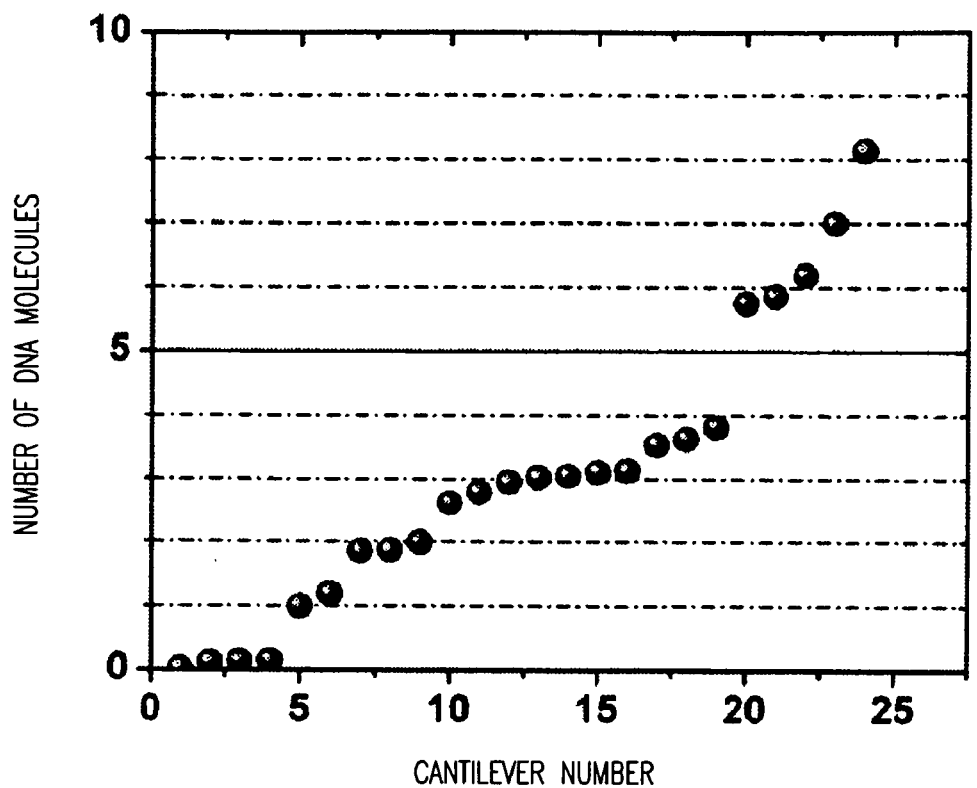
FIGS. 19A and 19B are respective plots of the number of molecules on various cantilevers, and optical detector output versus frequency according to an example embodiment.

FIG. 19A illustrates the response of various cantilevers to the mass loading caused by the DNA binding and by the non-specific binding during control experiments. With the most sensitive cantilever we can detect the binding of a single molecule. For the detection and counting of small numbers of dsDNA molecules, we have utilized cantilevers of lengths l=3.5 μm to sample a 0.03 ng/μl DNA concentration solution for 90 sec and 120 sec immobilization times as shown in FIG. 20.

Figure 19B:
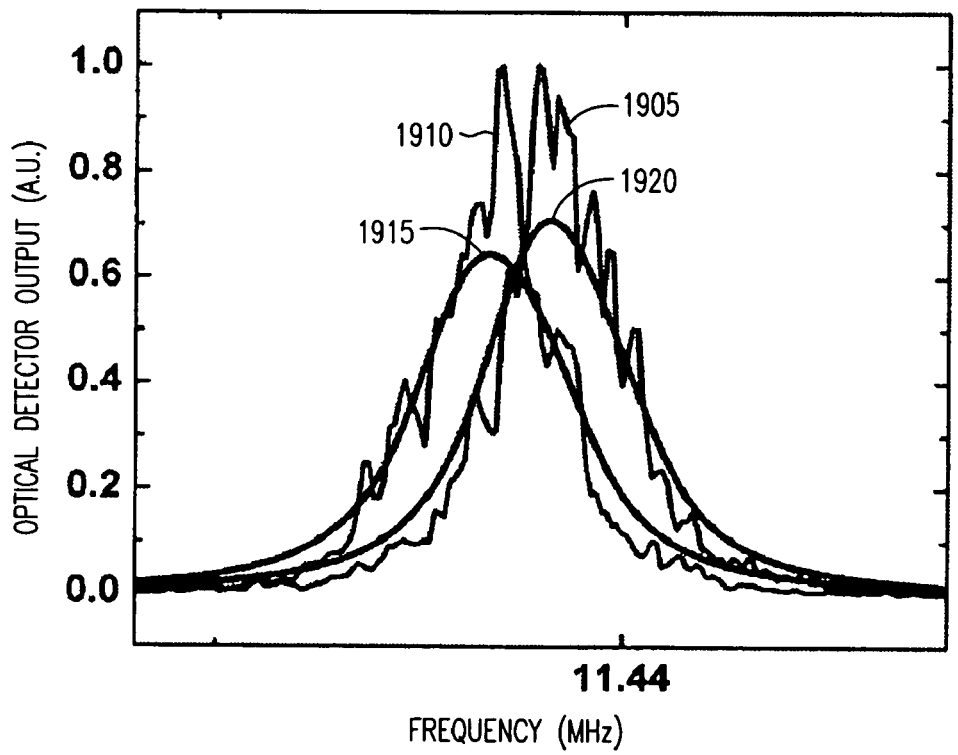

FIG. 19A represents a response of l=3.5 μm cantilevers to the loading effects of 0.03 ng/μl concentration of dsDNA. FIG. 19B shows frequency spectra before 1905 and after 1910 the binding events show a frequency shift due to a single dsDNA molecule bound to the Au surface of the cantilever. Enhancement of the mechanical factor (Q~7800) can be attributed to improved vacuum conditions and minimization of out-gassing collectively causing suppressed viscous damping. Even though the data curve appears rough, the calculated uncertainty from the Lorentzian fit 1915, 1920 was ±8.33 Hz.

The substantial and reproducible shift in the natural frequency of individual oscillators strongly suggests that integration of Au dots could be used as specific binding surfaces for a range of biomolecules through the thiol chemistry. Overall, our data indicate that NEMS oscillators with prefabricated biomolecular tethering sites are good candidates for detection of single biomolecules.

The devices we described may be made by lithographic techniques that can form a large number of nearly identical sensing elements in a configuration that integrates well with systems architectures. The optical drive and motion transduction approach allows for rapid interrogation of array elements in a matter similar to conventional binding array technologies. The sensitivity of the devices are sufficient to detect the binding of a single large biomolecule without labeling. Moreover, increased sensitivity would be expected for devices further miniaturized by available high-resolution lithographic methods. Because of the localized binding mass and resulting calibrated response, precise mass quantification can be accomplished for identically immobilized elements and enumeration of discrete bound molecules. Combining the mass detection technique with immunospecific or other optical labeling techniques allows for additional discrimination between different bound compounds. We have incorporated similar mechanical devices in optically accessible microfluidic channels and we anticipate that it is in this configuration that high-resolution nanomechanical sensors would be utilized in diagnostic or sensor systems.

CONCLUSION

NEMS oscillators have been fabricated with integrated circular Au contacts with subattogram mass detection sensitivity. The contacts server as precisely located binding sites. Shaping of oscillators may be done to enhance the optical detection of the motion of the oscillators while maintaining a low mass and proper spring constant of the resonant structure required for sensitive mass detection.

Arrays of surface micromachined oscillators with precisely positioned gold anchors may also be provided. The incorporation of prefabricated catalyzing adsorption sites allows spatial control of chemical surface functionality for the detection of analytes of interest. Results from study of fabricated devices aid in the design of high-sensitivity mass sensors capable of quantitative mass detection.

Mass loading effects of selectively immobilized DNP-PEG4-C11 thiolate molecules to prefabricated Au contacts on the surface of the NEMS resonator are highlighted. The size of the circular Au element varied from d=50 to 400 nm, but may be outside that range in various embodiments. Analytic calculations show that the most sensitive position of gold tethering site is near the free end of a cantilever oscillator and at the midpoint of a bridge oscillator at the point where the vibrational amplitude is maximum.

The observed shift in the natural frequency of the resonator was correlated to analytical models. The theoretical frequency shifts calculated by using Euler-Bernoulli are approximately in accordance with the experimental data. As verified by finite element analysis, when rotational inertia corrections are applied the approach allows for a more accurate determination of the eigenfrequency.

Discrepancies based on the simplified model are ascribed to subtle variations in the complex morphology of the Au element which lead to modifications of the nucleation sites for the thiolate SAM. Control experiments utilizing oscillators without Au contacts, did not show a shift in the natural frequency signifying selectivity of the thiolate binding. 0.39 ag is estimated as the smallest resolvable mass for an oscillator with dimensions of l=4 μm, w=500 nm, and t=160 nm, with a 1 μm×1 μm paddle. Based on mass sensitivity calculations, this technique presents an opportunity for detection of a single biomolecule adsorbed on the surface of the NEMS oscillator. Further tailoring of device dimensions and mechanical properties may additionally extend the mass sensitivity to the zeptogram regime.

Many embodiments have been described with corresponding process parameters and dimensional limitations. One of skill in the art will be able to significantly modify many of such dimensions and parameters without departing from the scope of the claims. The incorporation of prefabricated catalyzing adsorption sites allows spatial control of chemical surface functionality for the detection of analytes of interest. Many different types of adsorption sites may be used other than gold to detect many different types of analytes. The ability to fabricate such adsorption sites at desired locations may provide increased sensitivity to small masses of desired materials to be detected.

The Abstract is provided to comply with 37 C.F.R. § 1.72 (b) to allow the reader to quickly ascertain the nature and gist of the technical disclosure. The Abstract is submitted with the understanding that it will not be used to interpret or limit the scope or meaning of the claims.

The invention claimed is:

1. A MEMs device comprising:
   a MEMs oscillator;
   a catalyzing adsorption site supported by the oscillator, such that the sites provide control of chemical surface functionality for the detection of desired analytes, wherein the site is adapted to obtain a desired oscillator resonant frequency shift, such shift representing the difference between a site with attached analyte and without attached analyte.

2. The MEMs device of claim 1 wherein the catalyzing adsorption site comprises a gold anchor.

3. The MEMs device of claim 2 wherein the catalyzing adsorption site comprises provide control of chemical surface functionality for detection of desired analytes.

4. The MEMs device of claim 2 wherein the catalyzing adsorption site further comprises thiolate molecules coupled to the gold anchor.

5. The MEMs device of claim 1 wherein the catalyzing adsorption site comprises a self assembled monolayer.

6. The MEMs device of claim 5 wherein the monolayer comprises a supermolecular hierarchical organization of interlocking components.

7. The MEMs device of claim 6 wherein the monolayer comprises tail group functionalities selected from the group consisting of $CH_3$, OH, COOH, $CH=CH_2$, $C\equiv CH$, and $CF_3$.

8. The MEMs device of claim 6 wherein the monolayer is a circular area approximately between 50 and 400 nm in diameter.

9. The MEMs device of claim 1 wherein the oscillator comprises a nanomechanical cantilever beam.

10. The MEMs device of claim 1 wherein the oscillator comprises a dual clamped nanomechanical beam.

11. The MEMs device of claim 1 wherein the oscillator comprises a nanomechanical beam having a paddle shaped portion supporting the catalyzing adsorption site.

12. The MEMS device of claim 1 wherein the catalyzing adsorption site has a size selected to obtain frequency response characteristics optimized for detection of a desired analyte.

13. The MEMS device of claim 1 wherein the oscillator is vacuum encapsulated to increase frequency response characteristics.

14. A device comprising:
    a vibrating beam supported by a substrate;
    a catalyzing adsorption site supported by the oscillator and is shaped and positioned on the oscillator to obtain a desired oscillator resonant frequency shift, such shift representing the difference between a site with attached analyte and without an attached analyte for sensitive mass detection.

15. The device of claim 14 and further comprising a thiolate self-assembled monolayer (SAM) coupled to the adsorption site.

16. The device of claim 15 wherein the frequency of vibration measurably varies in response to attogram masses attached to the SAM.

17. The device of claim 14 wherein the beam is a cantilevered beam having a pad positioned proximate a free end of the cantilevered beam.

18. The device of claim 17 wherein the catalyzing adsorption site is positioned on the pad.

19. The device of claim 14 wherein the beam has a length of less than approximately 20 um.

20. The device of claim 14 wherein the beam is a double clamped beam having a pad positioned approximately halfway between the clamped ends.

21. A device comprising:
    a microelectromechanical polycrystalline silicon beam resonator having a free end with a paddle and a clamped end supported by a substrate;
    a catalyzing adsorption site supported by the paddle adapted to obtain a desired oscillator resonant frequency shift, such shift representing the difference between a site with an attached analyte and without attached analyte.

22. The device of claim 21 wherein the paddle is approximately 1 μm by 1 μm with a gold pad formed thereon.

* * * * *